(12) United States Patent
McDonald

(10) Patent No.: US 11,471,684 B2
(45) Date of Patent: Oct. 18, 2022

(54) USER-WEIGHTED CLOSED LOOP ADJUSTMENT OF NEUROMODULATION TREATMENT

(71) Applicant: Boston Scientific Neuromodulation Corporation, Valencia, CA (US)

(72) Inventor: Matthew Lee McDonald, Pasadena, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 194 days.

(21) Appl. No.: 16/778,367

(22) Filed: Jan. 31, 2020

(65) Prior Publication Data
US 2020/0282218 A1    Sep. 10, 2020

Related U.S. Application Data

(60) Provisional application No. 62/813,262, filed on Mar. 4, 2019.

(51) Int. Cl.
*A61N 1/36* (2006.01)
*G16H 40/67* (2018.01)
*G06N 3/02* (2006.01)

(52) U.S. Cl.
CPC ..... *A61N 1/36132* (2013.01); *A61N 1/36071* (2013.01); *A61N 1/36078* (2013.01);
(Continued)

(58) Field of Classification Search
CPC ............ A61N 1/36132; A61N 1/36071; A61N 1/36078; A61N 1/36096; A61N 1/36175; A61N 1/37235
See application file for complete search history.

(56) References Cited

U.S. PATENT DOCUMENTS 7,463,927 B1    12/2008  Chaouat
7,647,117 B2 *  1/2010   Bauhahn ............ A61N 1/37247
                                                     607/59
(Continued)

FOREIGN PATENT DOCUMENTS

CN        113795298 A    12/2021
WO    WO-2020180433 A1   9/2020

OTHER PUBLICATIONS

"International Application Serial No. PCT/US2020/016090, International Preliminary Report on Patentability dated Sep. 16, 2021", 8 pgs.

(Continued)

*Primary Examiner* — Mallika D Fairchild
(74) *Attorney, Agent, or Firm* — Schwegman Lundberg & Woessner, P.A.

(57) ABSTRACT

Systems and techniques are disclosed to generate programming parameters and modifications during closed-loop adjustment of an implantable neurostimulation device treatment programming, through the identification and application of weights determined from user input indications and rankings of therapy objectives. In an example, a system to generate programming values of a neurostimulation device performs operations that: obtains human input which indicates multiple therapy objectives for neurostimulation treatment of a human patient; operates a model (such as an artificial intelligence model) to determine parameter outputs for programming of the neurostimulation device; identifies weights, based on the therapy objectives, usable in the model; produces a composite output from the model, by applying the identified weights to a combination of the parameter outputs of the programming model; and the resulting composite output provides neurostimulation device (Continued)

programming values for neurostimulation treatment designed to address the therapy objectives.

20 Claims, 10 Drawing Sheets

(52) U.S. Cl.
CPC ..... *A61N 1/36096* (2013.01); *A61N 1/36175* (2013.01); *G06N 3/02* (2013.01); *G16H 40/67* (2018.01)

(56) References Cited

U.S. PATENT DOCUMENTS

| | | |
|---|---|---|
| 2005/0006001 A1 | 3/2005 | Goetz |
| 2005/0060010 A1* | 3/2005 | Goetz ................. A61N 1/3605 607/48 |
| 2014/0350634 A1 | 11/2014 | Grill et al. |
| 2016/0287877 A1* | 10/2016 | Jung .................... A61N 1/3611 |
| 2017/0056642 A1 | 3/2017 | Moffitt et al. |
| 2017/0189685 A1 | 7/2017 | Steinke et al. |
| 2018/0043172 A1 | 2/2018 | Serrano Carmona |
| 2018/0117334 A1 | 5/2018 | Jung |
| 2018/0193651 A1 | 7/2018 | Annoni et al. |

OTHER PUBLICATIONS

"International Application Serial No. PCT/US2020/016090, International Search Report dated Apr. 28, 2020", 5 pgs.

"International Application Serial No. PCT/US2020/016090, Written Opinion dated Apr. 28, 2020", 6 pgs.

"Australian Application Serial No. 2020233573, First Examination Report dated Aug. 8, 2022", 3 pgs.

* cited by examiner

USER-WEIGHTED CLOSED LOOP ADJUSTMENT OF NEUROMODULATION TREATMENT

CLAIM OF PRIORITY

This application claims the benefit of priority under 35 U.S.C. § 119(e) of U.S. Provisional Patent Application Ser. No. 62/813,262, filed on Mar. 4, 2019, which is herein incorporated by reference in its entirety.

TECHNICAL FIELD

The present disclosure relates generally to medical devices, and more particularly, to systems, devices, and methods for electrical stimulation programming techniques using artificial intelligence models and related mechanisms for closed loop adjustment, to control implanted electrical stimulation for pain treatment and/or management.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system.

A neurostimulation system can be used to electrically stimulate tissue or nerve centers to treat nervous or muscular disorders. For example, an SCS system may be configured to deliver electrical pulses to a specified region of a patient's spinal cord, such as particular spinal nerve roots or nerve bundles, to produce an analgesic effect that masks pain sensation, or to produce a functional effect that allows increased movement or activity of the patient. Other forms of neurostimulation may include a DBS system which uses similar pulses of electricity at particular locations in the brain to reduce symptoms of essential tremors, Parkinson's disease, psychological disorders, or the like.

While modern electronics can accommodate the need for generating and delivering neurostimulation energy in a variety of forms, the capability of a neurostimulation system depends on its post-manufacturing programmability to a great extent. One limiting factor for existing applications of neurostimulation therapies is that, even if a number of advanced programs can be applied by a neurostimulation device, patients often only end up using very few of the available treatments suggested by a clinician or other medical professional.

Many approaches for neurostimulation programming and customization have employed an open-loop design, with static stimulation parameters or programs being introduced, deployed, tested, and adjusted through clinician programming and patient-to-clinician feedback. Although some neurostimulation devices provide the capability to enable a patient to switch between programs, modify programs, or change the level of a certain stimulation effect, the amount of control given to the patient is typically limited to minor changes or the selection among pre-determined programs.

SUMMARY

The following Summary provides examples as an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

Example 1 is a system for use to generate programming values for a neurostimulation device, the system comprising: at least one processor; and at least one memory device comprising instructions, which when executed by the processor, cause the processor to perform operations that: obtain input indicating multiple therapy objectives, the therapy objectives being provided by a human patient for treatment with the neurostimulation device; operate an artificial intelligence neurostimulation programming model, the programming model configured to determine parameter outputs for programming of the neurostimulation device; identify weights for use in the programming model, based on the multiple therapy objectives indicated in the input; and produce a composite output from the programming model, by applying the identified weights to a combination of the parameter outputs of the programming model, wherein the composite output is used for programming the neurostimulation device for the treatment of the human patient.

In Example 2, the subject matter of Example 1 includes, the processor further to perform operations that: communicate programming parameters of the composite output to the neurostimulation device.

In Example 3, the subject matter of Examples 1-2 includes, the programming model being implemented as an artificial neural network or as a machine learning classifier.

In Example 4, the subject matter of Example 3 includes, the programming model being implemented as a deep neural network that includes a plurality of processing layers, wherein the identified weights are applied at an output layer of the deep neural network.

In Example 5, the subject matter of Examples 1-4 includes, the processor further to perform operations that: obtain user feedback, the user feedback indicating user-indicated efficacy of the programming of the neurostimulation device using the composite output, based on the multiple therapy objectives; and generate updated weights for use in the programming model, the updated weights produced from changes to the identified weights based on the user feedback.

In Example 6, the subject matter of Examples 1-5 includes, the processor further to perform operations that: obtain sensor data feedback, the sensor data feedback indicating a measurement related to one or more of the multiple therapy objectives; and generate updated weights for use in the programming model, the updated weights produced from changes to the identified weights based on the sensor data feedback.

In Example 7, the subject matter of Examples 1-6 includes, the input further indicating a rating value associated with each of the multiple therapy objectives, wherein the respective rating values associated with the multiple therapy objectives are used to determine values of the identified weights for use in the programming model.

In Example 8, the subject matter of Examples 1-7 includes, the multiple therapy objectives being selected from a set of available therapy objectives, and the multiple therapy objectives being selected based on an identification including one or more of: patient identification of one or more therapy types to produce with the programming model, clinician identification of one or more therapy types to produce with the programming model, or algorithm identification of one or more therapy types to produce with the programming model.

In Example 9, the subject matter of Examples 1-8 includes, the multiple therapy objectives including a combination of at least two therapy types selected from among: pain management, sleep quality, medication management, mood improvement, depression reduction, or activity capabilities.

In Example 10, the subject matter of Examples 1-9 includes, the processor further to perform operations that: generate activity, behavior, or therapy recommendations for the human patient, based on the multiple therapy objectives indicated in the input.

In Example 11, the subject matter of Examples 1-10 includes, the processor further to perform operations that: obtain input indicating variations to the multiple therapy objectives, the variations to the multiple therapy objectives being provided by a clinician associated with treatment of the human patient; and perform balancing of the therapy objectives with the variations to the therapy objectives, based on a comparison between the variations to the therapy objectives provided by the clinician and the therapy objectives provided by the human patient; wherein the identified weights are produced from the balancing of the therapy objectives with the variations to the therapy objectives.

In Example 12, the subject matter of Example 11 includes, the input provided by the clinician being obtained in a clinician graphical user interface, the input provided by the human patient being obtained in a patient graphical user interface.

In Example 13, the subject matter of Examples 1-12 includes, the composite output being utilized as a parameter of a neurostimulation program for the neurostimulation device, the instructions further to cause the processor to: identify programming values for at least one neurostimulation programming parameter in the neurostimulation program based on the composite output; wherein the identified programming values specify operation of the neurostimulation program for one or more of: pulse patterns, pulse shapes, a spatial location of pulses, waveform shapes, or a spatial location of waveform shapes, for modulated energy provided with a plurality of leads of the neurostimulation device.

Example 14 is a machine-readable medium including instructions, which when executed by a machine, cause the machine to perform the operations of the system of any of the Examples 1 to 13.

Example 15 is a method to perform the operations of the system of any of the Examples 1 to 13.

Example 16 is a device adapted for use to generate programming values for a neurostimulation device, the device comprising: at least one processor and at least one memory; input and weighting control circuitry, operable with the processor and the memory, the input and weighting control circuitry configured to: obtain input indicating multiple therapy objectives, the therapy objectives being provided by a human patient for treatment with the neurostimulation device; operate an artificial intelligence neurostimulation programming model, the programming model configured to determine parameter outputs for programming of the neurostimulation device; identify weights for use in the programming model, based on the multiple therapy objectives indicated in the input; and generate a composite output from the programming model, by applying the identified weights to a combination of the parameter outputs of the programming model; neurostimulation programming circuitry, in operation with the at least one processor and the at least one memory, configured to: produce parameter programming values for programming the neurostimulation device, based on the composite output, for the treatment of the human patient according to the therapy objectives.

In Example 17, the subject matter of Example 16 includes, the neurostimulation programming circuitry further configured to communicate programming parameters of the composite output to the neurostimulation device.

In Example 18, the subject matter of Examples 16-17 includes, the programming model being implemented as an artificial neural network or as a machine learning classifier.

In Example 19, the subject matter of Examples 16-18 includes, the input and weighting control circuitry further configured to: obtain user feedback, the user feedback indicating user-indicated efficacy of the programming of the neurostimulation device using the composite output, based on the multiple therapy objectives; and generate updated weights for use in the programming model, the updated weights produced from changes to the identified weights based on the user feedback.

In Example 20, the subject matter of Examples 16-19 includes, the input and weighting control circuitry further configured to: obtain sensor data feedback, the sensor data feedback indicating a measurement related to one or more of the multiple therapy objectives; and generate updated weights for use in the programming model, the updated weights produced from changes to the identified weights based on the sensor data feedback.

In Example 21, the subject matter of Examples 16-20 includes, the input further indicating a rating value associated with each of the multiple therapy objectives, wherein the respective rating values associated with the multiple therapy objectives are used to determine values of the identified weights for use in the programming model.

In Example 22, the subject matter of Examples 16-21 includes, the multiple therapy objectives being selected from a set of available therapy objectives, wherein the multiple therapy objectives are selected based on an identification including one or more of: patient identification of one or more therapy types to produce with the programming model, clinician identification of one or more therapy types to produce with the programming model, or algorithm identification of one or more therapy types to produce with the programming model.

In Example 23, the subject matter of Examples 16-22 includes, the multiple therapy objectives including a combination of at least two therapy types selected from among: pain management, sleep quality, medication management, mood improvement, depression reduction, or activity capabilities.

In Example 24, the subject matter of Examples 16-23 includes, the input and weighting control circuitry further configured to: obtain input indicating variations to the multiple therapy objectives, the variations to the multiple therapy objectives being provided by a clinician associated with treatment of the human patient; and perform balancing of the therapy objectives with the variations to the therapy objectives, based on a comparison between the variations to the therapy objectives provided by the clinician and the therapy objectives provided by the human patient; wherein the identified weights are produced from the balancing of the therapy objectives with the variations to the therapy objectives; and wherein the input provided by the clinician is obtained in a clinician graphical user interface, and wherein the input provided by the human patient is obtained in a patient graphical user interface.

In Example 25, the subject matter of Examples 16-24 includes, the composite output being utilized as a parameter of a neurostimulation program for the neurostimulation device, wherein the neurostimulation programming circuitry is further configured to: identify programming values for at least one neurostimulation programming parameter in the neurostimulation program based on the composite output; wherein the identified programming values specify operation of the neurostimulation program for one or more of: pulse patterns, pulse shapes, a spatial location of pulses, waveform shapes, or a spatial location of waveform shapes, for modulated energy provided with a plurality of leads of the neurostimulation device.

Example 26 is a method for use to generate programming values for a neurostimulation device, the method comprising a plurality of operations executed with at least one processor of an electronic device, the plurality of operations comprising: receiving input indicating multiple therapy objectives, the therapy objectives being provided by a human patient for treatment with the neurostimulation device; executing an artificial intelligence neurostimulation programming model, the programming model configured to determine parameter outputs for programming of the neurostimulation device; identifying weights for use in the programming model, based on the multiple therapy objectives indicated in the input; generating a composite output from the programming model, by applying the identified weights to a combination of the parameter outputs of the programming model, wherein the composite output is used for programming the neurostimulation device for the treatment of the human patient.

In Example 27, the subject matter of Example 26 includes, communicating programming parameters of the composite output to the neurostimulation device.

In Example 28, the subject matter of Examples 26-27 includes, the programming model being implemented as an artificial neural network or as a machine learning classifier.

In Example 29, the subject matter of Examples 26-28 includes, obtaining user feedback, the user feedback indicating user-indicated efficacy of the programming of the neurostimulation device using the composite output, based on the multiple therapy objectives; and generating updated weights for use in the programming model, the updated weights produced from changes to the identified weights based on the user feedback.

In Example 30, the subject matter of Examples 26-29 includes, obtaining sensor data feedback, the sensor data feedback indicating a measurement related to one or more of the multiple therapy objectives; and generating updated weights for use in the programming model, the updated weights produced from changes to the identified weights based on the sensor data feedback.

In Example 31, the subject matter of Examples 26-30 includes, the input further indicating a rating value associated with each of the multiple therapy objectives, wherein the respective rating values associated with the multiple therapy objectives are used to determine values of the identified weights for use in the programming model.

In Example 32, the subject matter of Examples 26-31 includes, the multiple therapy objectives being selected from a set of available therapy objectives, and the multiple therapy objectives being selected based on an identification including one or more of: patient identification of one or more therapy types to produce with the programming model, clinician identification of one or more therapy types to produce with the programming model, or algorithm identification of one or more therapy types to produce with the programming model.

In Example 33, the subject matter of Examples 26-32 includes, the multiple therapy objectives including a combination of at least two therapy types selected from among: pain management, sleep quality, medication management, mood improvement, depression reduction, or activity capabilities.

In Example 34, the subject matter of Examples 26-33 includes, obtaining input indicating variations to the multiple therapy objectives, the variations to the multiple therapy objectives being provided by a clinician associated with treatment of the human patient; and performing balancing of the therapy objectives with the variations to the therapy objectives, based on a comparison between the variations to the therapy objectives provided by the clinician and the therapy objectives provided by the human patient; wherein the identified weights are produced from the balancing of the therapy objectives with the variations to the therapy objectives; and wherein the input provided by the clinician is obtained in a clinician graphical user interface, and wherein the input provided by the human patient is obtained in a patient graphical user interface.

In Example 35, the subject matter of Examples 26-34 includes, the composite output utilized as a parameter of a neurostimulation program for the neurostimulation device, the operations further comprising: identifying programming values for at least one neurostimulation programming parameter in the neurostimulation program based on the composite output; wherein the identified programming values specify operation of the neurostimulation program for one or more of: pulse patterns, pulse shapes, a spatial location of pulses, waveform shapes, or a spatial location of waveform shapes, for modulated energy provided with a plurality of leads of the neurostimulation device.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
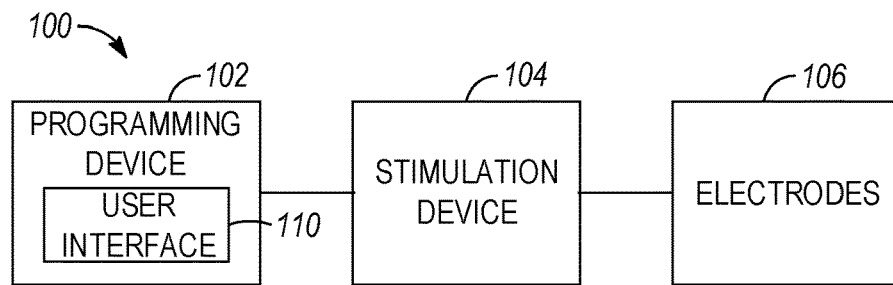
FIG. 1 illustrates, by way of example, an embodiment of a neurostimulation system.

This document discusses various techniques that can generate and determine programming values of an implantable electrical neurostimulation device, for the treatment of pain or related physiological conditions in a human subject (e.g., a patient). As an example, various systems and methods are described to generate, identify, implement, or adjust parameters of neurostimulation treatment in a closed-loop therapy approach based on user-provided therapy indications, programming selections, and feedback. These systems and methods are designed to consider the patient's intended result of treatment (referred to herein as a therapy "objective"), and to balance the type and value of multiple therapy objectives, so that programming results of a neurostimulation device may be improved and customized to a particular patient using appropriate weighting values.

With many existing approaches of neurostimulation treatment involving clinician-based programming, the patient ends up applying programs that are not customized to the patient or provide a best fit for the patient's desired therapy objectives. The present techniques and systems improve this scenario through the use of input and weighting control logic (implemented, among other locations, in a program modeling system and closed loop programming system) which evaluates different types and amounts of patient-specified therapy objectives. In various examples, the input and weighting control logic is designed to be integrated with existing programming workflows or operations of intelligent or closed-loop neuromodulation programming systems, including those implementing aspects of artificial intelligence (AI), such as machine learning, neural networks, decision trees, and the like.

As discussed herein, therapy objectives may be determined from patient inputs that indicate specific types and amounts of patient-specific directives for addressing a particular condition or symptom, such as an amount of pain reduction, sleep improvement, medication management, mood improvement or depression reduction, activity improvements, and the like, and quantified values (e.g., rankings, scores, percentages, etc.) to emphasize or control such therapy objectives. The programming outputs that are produced by the input and weighting control logic are intended to achieve a proper balance among multiple treatment objectives, based on the user inputs and directives, and based on the efficacy of neurostimulation programming capabilities to achieve the multiple treatment objectives.

In particular, the following approaches of input and weighting control may modify the operation of a predictive or classifying AI model, so that the AI model may produce usable outputs for neurostimulation programming having a suitable balance of multiple therapy objectives. In contrast, conventional models and programing methods, including the use of models designed for generating parameters in well-confined settings of neurostimulation therapy, are often designed to produce a single classification or model output that is optimized to a single condition (e.g., reducing perceived pain). Such models are often trained from training data that is selected or labeled to converge at a certain outcome (e.g., pain reduction) experienced among multiple patients. Such models do not provide the capability to allow the customization or variability of multiple objectives, nor do such models consider the tradeoffs in programming when a neurostimulation output for a single treatment objective (for instance, a neurostimulation electrical pulse which achieves a significant pain reduction may interfere with other treatment objectives such as mobility and range of motion). Thus, a patient who wishes to achieve multiple treatment objectives may be unable to utilize current forms of AI models and decision logic which produces fixed classification outputs.

The presently described input and weighting control mechanisms enables the adaptation of neurostimulation parameters based on direct user feedback and specifications regarding therapy objectives. The input and weighting control allows the selection and emphasis of a single treatment objective or multiple treatment objectives that can be used to balance or combine treatment results. The input and weighting control may use the user-specified treatment objectives to produce weights for use within processing operations of algorithms and models, that enable composite outputs from such algorithms and models by adjusting weighting or modifying a multivariate processing pathway. As a simplified use case, the input and weighting control may enable an AI-assisted generation of a neurostimulation program that emphasizes neurostimulation outputs to provide therapeutic benefits for both sleep and activity improvement; or in both opioid reduction and pain management; or any combination of multiple therapy objectives.

Although many of the following examples refer to multiple therapy objectives, the input and weighting control may also provide a mechanism by which a single therapy objective may be emphasized or enhanced, such as to address scenarios where a particular objective (e.g., mobility) conflicts with the type of neurostimulation treatment deployed for other conditions (e.g., pain reduction). As a result, the input and weighting control provides an approach by which many variations in user input can be considered, including in closed loop AI models and feedback-based programming scenarios.

In an example, the input and weighting control identifies a set of weights, for use in a neurostimulation programming model, which emphasize the therapy objectives expressed from human user input. These identified weights are applied to dynamically select, adjust, and modify neurostimulation treatment outputs (e.g., neurostimulation device programming parameters), including from the creation of composite outputs from the programming model. After the composite outputs from the programming model are implemented for use with a human patient, then additional selection, adjustment, and modification logic collects feedback from subsequent conditions and changes in the patient, to incorporate additional changes or adaptations that address the multiple therapy objectives. When implemented in a closed-loop programming system, the input and weighting control introduces an advanced level of control and customization for therapy which can greatly enhance a neurostimulation treatment regimen.

By way of example, operational parameters of the neurostimulation device which are generated or identified by the present systems and techniques may include amplitude, frequency, duration, pulse width, pulse type, patterns of neurostimulation pulses, waveforms in the patterns of pulses, and like settings with respect to the intensity, type, and location of neurostimulator output on individual or a plurality of respective leads. The neurostimulator may use current or voltage sources to provide the neurostimulator output, and apply any number of control techniques to modify the electrical simulation applied to anatomical sites or systems related to pain or analgesic effect. In various embodiments, a neurostimulator program may be defined or updated to indicate parameters that define spatial, temporal, and informational characteristics for the delivery of modulated energy, including the definitions or parameters of pulses of modulated energy, waveforms of pulses, pulse blocks each including a burst of pulses, pulse trains each including a sequence of pulse blocks, train groups each including a sequence of pulse trains, and programs of such definitions or parameters, each including one or more train groups scheduled for delivery. Characteristics of the waveform that are defined in the program may include, but are not limited to the following: amplitude, pulse width, frequency, total charge injected per unit time, cycling (e.g., on/off time), pulse shape, number of phases, phase order, interphase time, charge balance, ramping, as well as spatial variance (e.g., electrode configuration changes over time). It will be understood that based on the many characteristics of the waveform itself, a program may have many parameter setting combinations that would be potentially available for use.

In various embodiments, the present subject matter may be implemented using a combination of hardware and software designed to provide users such as patients, caregivers, clinicians, researchers, physicians, or others with the ability to generate, identify, select, implement, and update neurostimulation programs which achieve the indicated therapy objectives. The implementation of neurostimulation programs, particularly in a closed-loop system, may result in variation in the location, intensity, and type of defined waveforms and patterns in an effort to increase therapeutic efficacy and/or patient satisfaction for neurostimulation therapies, such as SCS and DBS therapies. While neurostimulation is specifically discussed as an example, the present subject matter may apply to any therapy that employs stimulation pulses of electrical or other forms of energy for treating chronic pain or like physiological or psychological conditions.

The delivery of neurostimulation energy that is discussed herein may be delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. Many current neurostimulation systems are programmed to deliver periodic pulses with one or a few uniform waveforms continuously or in bursts. However, neural signals may include more sophisticated patterns to communicate various types of information, including sensations of pain, pressure, temperature, etc. Accordingly, the following drawings provide an introduction to the features of an example neurostimulation system and how such programming may be accomplished through open-loop or closed-loop neurostimulation systems.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are selected or programmable by a clinical user, such as a physician or other caregiver who treats the patient using system 100; however, some of the parameters may also be provided in connection with closed-loop programming logic and adjustment. Programming device 102 provides the user with accessibility to implement, change, or modify the programmable parameters. In various embodiments, programming device 102 is configured to be communicatively coupled to stimulation device 104 via a wired or wireless link.

In various embodiments, programming device 102 includes a user interface 110 (e.g., a user interface embodied by a graphical, text, voice, or hardware-based user interface) that allows the user to set and/or adjust values of the user-programmable parameters by creating, editing, loading, and removing programs that include parameter combinations such as patterns and waveforms. These adjustments may also include changing and editing values for the user-programmable parameters or sets of the user-programmable parameters individually (including values set in response to a therapy efficacy indication). Such waveforms may include, for example, the waveform of a pattern of neurostimulation pulses to be delivered to the patient as well as individual waveforms that are used as building blocks of the pattern of neurostimulation pulses. Examples of such individual waveforms include pulses, pulse groups, and groups of pulse groups. The program and respective sets of parameters may also define an electrode selection specific to each individually defined waveform.

As described in more detail below with respect to the data flows in FIGS. 7 to 11, a user, e.g., the patient, or a clinician or other medical professional associated with the patient can provide inputs which are used by closed-loop programming logic to select, load, modify, and implement one or more parameters of a defined program for neurostimulation treatment, based on treatment objectives that are evaluated by an input and weighting processing approach. Based on the operation of a parameter identification model, which is modified by weighting values produced from the input and weighting, various logic or algorithm can determine which program or parameter change within a program is likely to produce an improvement for the treatment objectives specified by user input, such as to address pain, mobility, sleep disruption, and the like. Example parameters that can be implemented by a selected neurostimulation program include, but are not limited to the following: amplitude, pulse width, frequency, duration, total charge injected per unit time, cycling (e.g., on/off time), pulse shape, number of phases, phase order, interphase time, charge balance, ramping, as well as spatial variance (e.g., electrode configuration changes over time).

Figure 6:
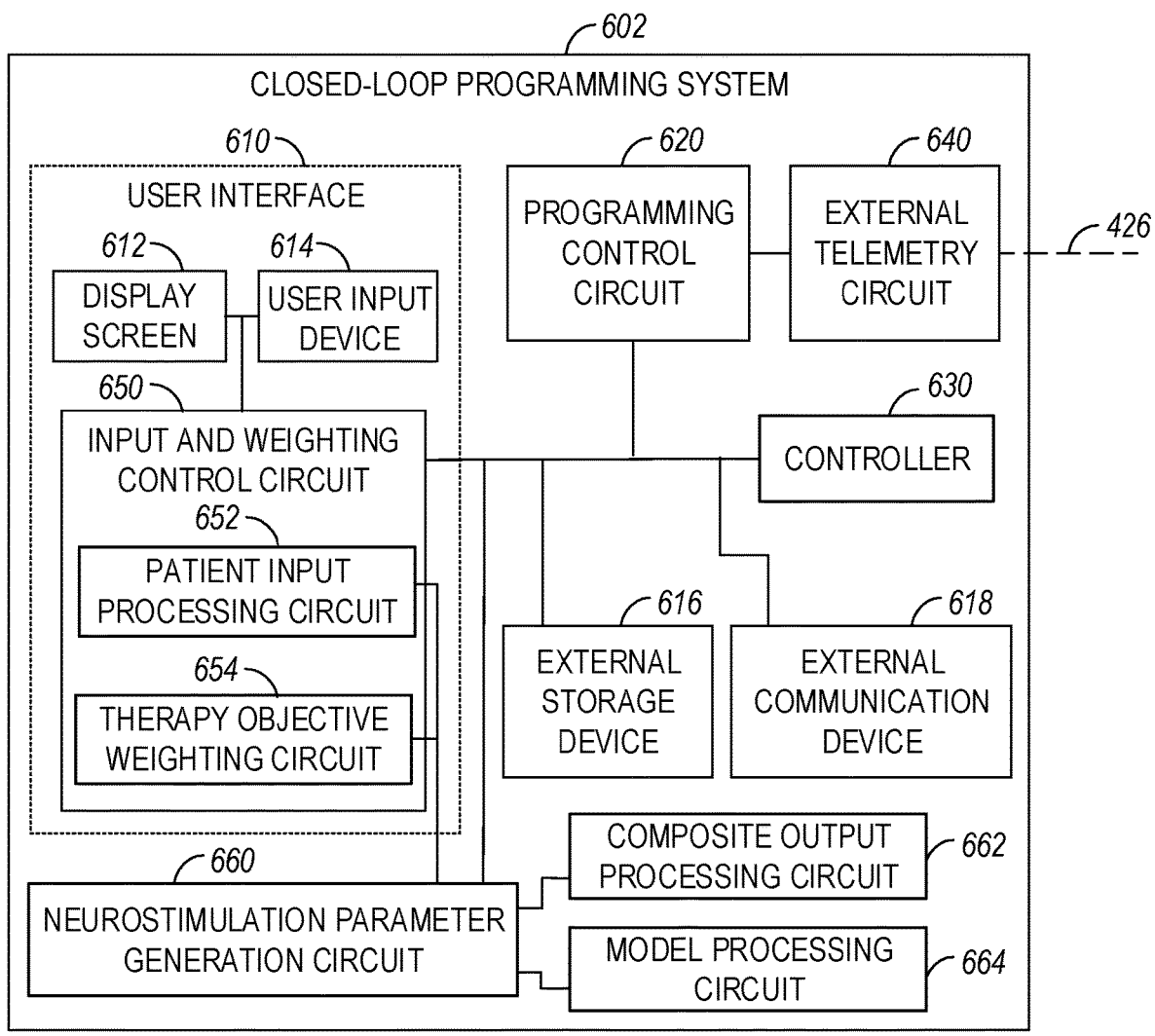
FIG. 6 illustrates, by way of example, an embodiment of a closed-loop programming device for a neurostimulation system, such as the implantable neurostimulation system of FIG. 4.

As detailed in FIG. 6, a controller, e.g., controller 630 of FIG. 6, can implement program(s) and parameter setting(s) to affect a specific neurostimulation waveform, pattern, or energy output, using a program or setting in storage, e.g., external storage device 616 of FIG. 6, or using settings communicated via an external communication device 618 of FIG. 6 corresponding to the selected program. The implementation of such program(s) or setting(s) may further define a therapy strength and treatment type corresponding to a specific pulse group, or a specific group of pulse groups, based on the specific program(s) or setting(s). As also described in more detail below with respect to FIG. 7 and thereafter, a program modeling system and closed loop programming system may operate to identify, select, produce, or generate this information in closed-loop feedback configuration, as user input and physiological sensor data is observed and monitored for further refinement. In addition to the use of closed-loop feedback, other forms of input from a clinician or the patient may also affect use and implementation of selected parameters or programs of the program modeling system and closed loop programming system, including in settings where a combination of dynamic (automatic) and manual control are involved.

Portions of the stimulation device 104, e.g., implantable medical device, or the programming device 102 can be implemented using hardware, software, or any combination of hardware and software. Portions of the stimulation device 104 or the programming device 102 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. The system 100 could also include a subcutaneous medical device (e.g., subcutaneous ICD, subcutaneous diagnostic device), wearable medical devices (e.g., patch-based sensing device), or other external medical devices.

Figure 2:
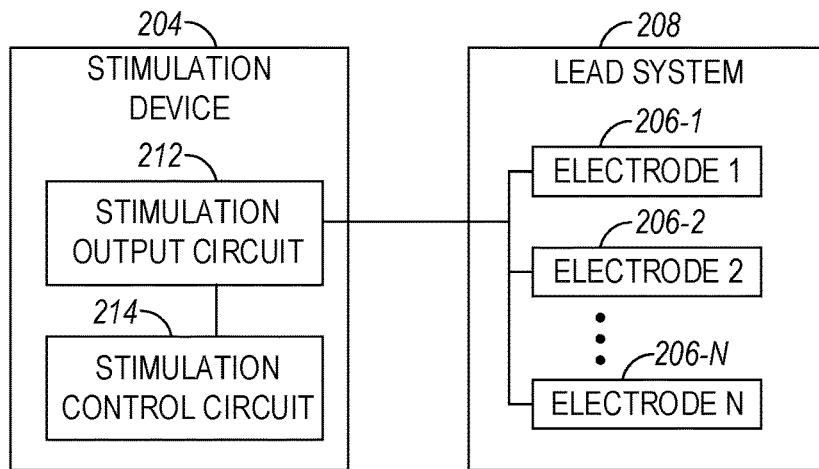
FIG. 2 illustrates, by way of example, an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100 of FIG. 1. Stimulation device 204 represents an embodiment of stimulation device 104 and includes a stimulation output circuit 212 and a stimulation control circuit 214. Stimulation output circuit 212 produces and delivers neurostimulation pulses, including the neurostimulation waveform and parameter settings implemented via a program selected or implemented with the user interface 110. Stimulation control circuit 214 controls the delivery of the neurostimulation pulses using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where $N \geq 2$. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes. Those of ordinary skill in the art will understand that the neurostimulation system 100 may include additional components such as sensing circuitry for patient monitoring and/or feedback control of the therapy, telemetry circuitry, and power. The neurostimulation system 100 may also integrate with other sensors, or such other sensors may independently provide information for use with programming of the neurostimulation system 100.

The neurostimulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses. Each electrode configuration, along with the electrical pulse parameters, can be referred to as a "modulation parameter" set. Each set of modulation parameters, including fractionalized current distribution to the electrodes (as percentage cathodic current, percentage anodic current, or off), may be stored and combined into a program that can then be used to modulate multiple regions within the patient.

The neurostimulation system may be configured to deliver different electrical fields to achieve a temporal summation of modulation. The electrical fields can be generated respectively on a pulse-by-pulse basis. For example, a first electrical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields can be rotated or cycled through multiple times under a timing scheme, where each field is implemented using a timing channel. The electrical fields may be generated at a continuous pulse rate, or as bursts of pulses. Furthermore, the interpulse interval (i.e., the time between adjacent pulses), pulse amplitude, and pulse duration during the electrical field cycles may be uniform or may vary within the electrical field cycle. Some examples are configured to determine a modulation parameter set to create a field shape to provide a broad and uniform modulation field such as may be useful to prime targeted neural tissue with sub-perception modulation. Some examples are configured to determine a modulation parameter set to create a field shape to reduce or minimize modulation of non-targeted tissue (e.g., dorsal column tissue). Various examples disclosed herein are directed to shaping the modulation field to enhance modulation of some neural structures and diminish modulation at other neural structures. The modulation field may be shaped by using multiple independent current control (MICC) or multiple independent voltage control to guide the estimate of current fractionalization among multiple electrodes and estimate a total amplitude that provide a desired strength. For example, the modulation field may be shaped to enhance the modulation of dorsal horn neural tissue and to minimize the modulation of dorsal column tissue. A benefit of MICC is that MICC accounts for various in electrode-tissue coupling efficiency and perception threshold at each individual contact, so that "hotspot" stimulation is eliminated.

The number of electrodes available combined with the ability to generate a variety of complex electrical pulses, presents a huge selection of available modulation parameter sets to the clinician or patient. For example, if the neurostimulation system to be programmed has sixteen electrodes, millions of modulation parameter value combinations may be available for programming into the neurostimulation system. Furthermore, some SCS systems have as many as thirty-two electrodes, which exponentially increases the number of modulation parameter value combinations available for programming. The implementation and use of a program modeling system and closed loop programming system as described further in FIGS. 7 to 10 and thereafter provides a mechanism for recommending and controlling programs and program parameters in a closed-loop fashion that still provides customization to the patient based on therapy objectives.

Figure 3:
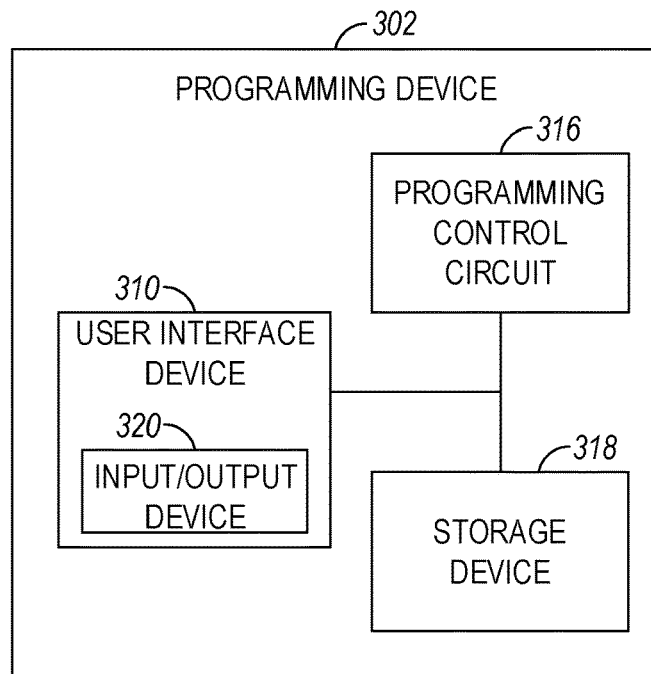
FIG. 3 illustrates, by way of example, an embodiment of a programming device, such as may be implemented in the neurostimulation system of FIG. 1.

FIG. 3 illustrates an embodiment of a programming device 302, such as may be implemented in neurostimulation system 100. Programming device 302 represents an embodiment of programming device 102 and includes a storage device 318, a programming control circuit 316, and a user interface device 310. Programming control circuit 316 generates the plurality of stimulation parameters that controls the delivery of the neurostimulation pulses according to the pattern of the neurostimulation pulses. The user interface device 310 represents an embodiment to implement the user interface 110.

In various embodiments, the user interface device 310 includes an input/output device 320 that is capable to receive user interaction and commands to load, modify, and implement neurostimulation programs and schedule delivery of the neurostimulation programs. In various embodiments, the input/output device 320 allows the user to create, establish, access, and implement respective parameter values of a neurostimulation program through graphical selection (e.g., in a graphical user interface output with the input/output device 320), or other graphical input/output relating to therapy objectives, efficacy of applied treatment, user feedback, and the like. In various examples, the user interface device 310 can receive user input to initiate or control the implementation of the programs or program changes which are recommended, modified, selected, or loaded through use of a closed loop programming system, described in more detail below.

In various embodiments, the input/output device 320 allows the patient user to apply, change, modify, or discontinue certain building blocks of a program and a frequency at which a selected program is delivered. In various embodiments, the input/output device 320 can allow the patient user to save, retrieve, and modify programs (and program settings) loaded from a clinical encounter, managed from the patient feedback computing device, or stored in storage device 318 as templates. In various embodiments, the input/output device 320 and accompanying software on the user interface device 310 allows newly created building blocks, program components, programs, and program modifications to be saved, stored, or otherwise persisted in storage device 318. Thus, it will be understood that the user interface device 310 may allow many forms of device operation and control, even as closed loop programming is occurring.

In one embodiment, the input/output device 320 includes a touchscreen. In various embodiments, the input/output device 320 includes any type of presentation device, such as interactive or non-interactive screens, and any type of user input device that allows the user to interact with a user interface to implement, remove, or schedule the programs. Thus, the input/output device 320 may include one or more of a touchscreen, keyboard, keypad, touchpad, trackball, joystick, and mouse. The logic of the user interface 110, the stimulation control circuit 214, and the programming control circuit 316, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
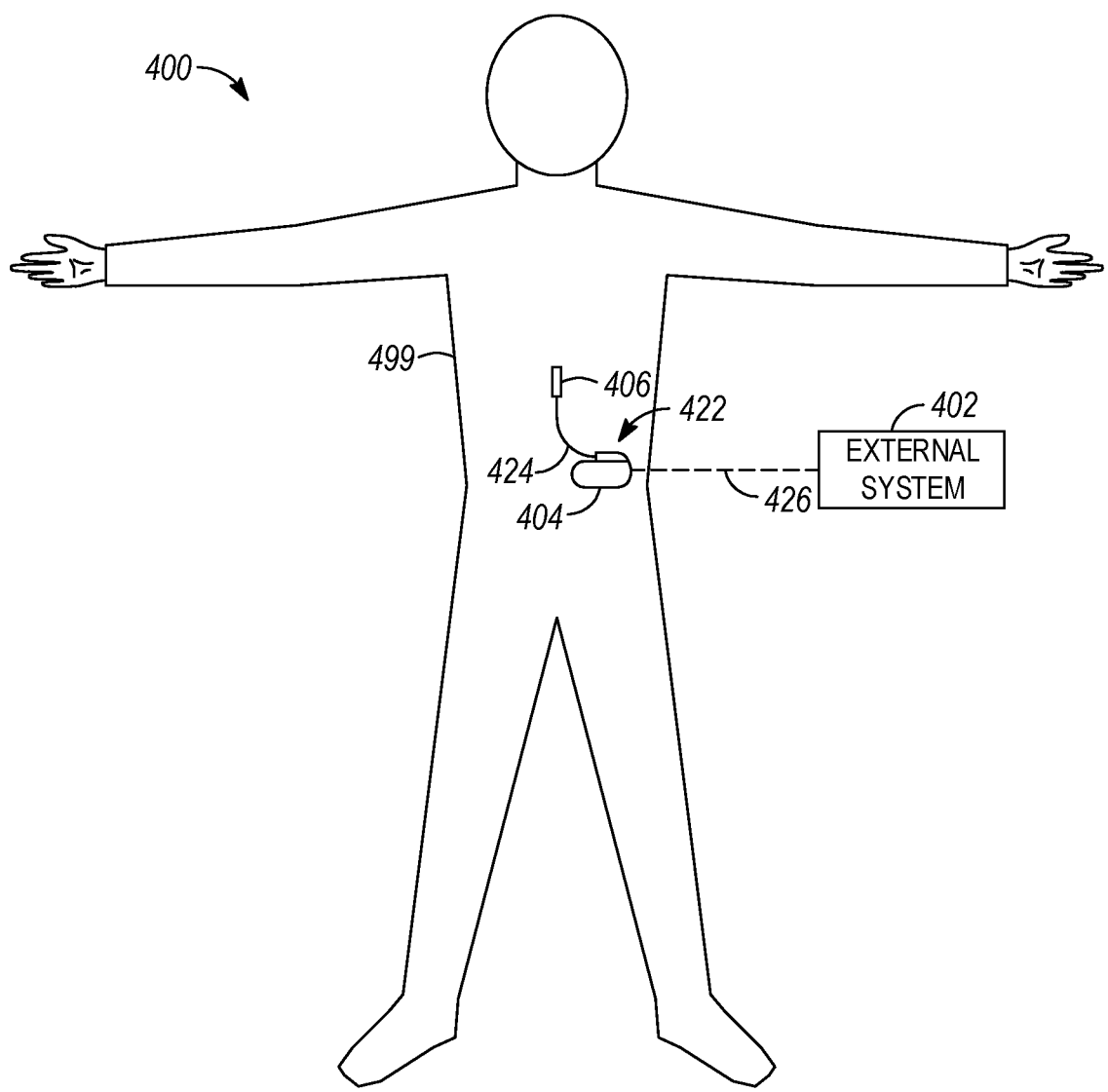
FIG. 4 illustrates, by way of example, an implantable neurostimulation system and portions of an environment in which the system may be used.

FIG. 4 illustrates an implantable neurostimulation system 400 and portions of an environment in which system 400 may be used. System 400 includes an implantable system 422, an external system 402, and a telemetry link 426 providing for wireless communication between an implantable system 422 and an external system 402. Implantable system 422 is illustrated in FIG. 4 as being implanted in the patient's body 499. The system is illustrated for implantation near the spinal cord. However, the neuromodulation system may be configured to modulate other neural targets.

Implantable system 422 includes an implantable stimulator 404 (also referred to as an implantable pulse generator, or IPG), a lead system 424, and electrodes 406, which represent an embodiment of the stimulation device 204, the lead system 208, and the electrodes 206, respectively. The external system 402 represents an embodiment of the programming device 302.

In various embodiments, the external system 402 includes one or more external (non-implantable) devices each allowing the user and/or the patient to communicate with the implantable system 422. In some embodiments, the external system 402 includes a programming device intended for the user to initialize and adjust settings for the implantable stimulator 404 and a remote control device intended for use by the patient. For example, the remote control device may allow the patient to turn the implantable stimulator 404 on and off and/or adjust certain patient-programmable parameters of the plurality of stimulation parameters. The remote control device may also provide a mechanism to receive and process feedback on the operation of the implantable neuromodulation system. Feedback may include metrics or an efficacy indication reflecting perceived pain, effectiveness of therapies, or other aspects of patient comfort or condition. Such feedback may be automatically detected from a patient's physiological state, collected from other sensors or devices (not shown), or manually obtained from user input entered in a user interface (such as with the user input scenarios discussed below).

As used herein, the terms "neurostimulator," "stimulator," "neurostimulation," and "stimulation" generally refer to the delivery of electrical energy that affects the neuronal activity of neural tissue, which may be excitatory or inhibitory; for example by initiating an action potential, inhibiting or blocking the propagation of action potentials, affecting changes in neurotransmitter/neuromodulator release or uptake, and inducing changes in neuro-plasticity or neurogenesis of tissue. It will be understood that other clinical effects and physiological mechanisms may also be provided through use of such stimulation techniques.

Figure 5:
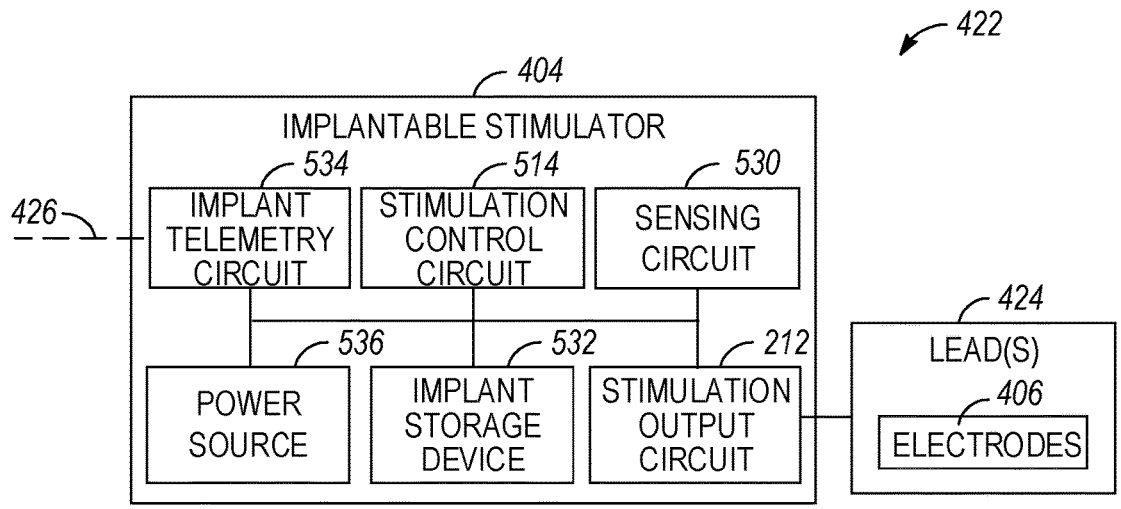
FIG. 5 illustrates, by way of example, an embodiment of an implantable stimulator and one or more leads of a neurostimulation system, such as the implantable neurostimulation system of FIG. 4.

FIG. 5 illustrates an embodiment of the implantable stimulator 404 and the one or more leads 424 of an implantable neurostimulation system, such as the implantable system 422. The implantable stimulator 404 may include a sensing circuit 530 used for an optional sensing capability, stimulation output circuit 212, a stimulation control circuit 514, an implant storage device 532, an implant telemetry circuit 534, and a power source 536. The sensing circuit 530, when included and needed, senses one or more physiological signals for purposes of patient monitoring and/or feedback control of the neurostimulation, including in the closed loop programming processes discussed herein. Examples of the one or more physiological signals includes neural and other signals each indicative of a condition of the patient that is treated by the neurostimulation and/or a response of the patient to the delivery of the neurostimulation.

The stimulation output circuit 212 is electrically connected to electrodes 406 through the one or more leads 424, and delivers each of the neurostimulation pulses through a set of electrodes selected from the electrodes 406. The stimulation output circuit 212 can implement, for example, the generating and delivery of a customized neurostimulation waveform (e.g., implemented from a parameter of a program selected with the closed-loop programming system) to an anatomical target of a patient.

The stimulation control circuit 514 represents an embodiment of the stimulation control circuit 214 and controls the delivery of the neurostimulation pulses using the plurality of stimulation parameters specifying the pattern of the neurostimulation pulses. In one embodiment, the stimulation control circuit 514 controls the delivery of the neurostimulation pulses using the one or more sensed physiological signals and processed input from patient feedback interfaces. The implant telemetry circuit 534 provides the implantable stimulator 404 with wireless communication with another device such as a device of the external system 402, including receiving values of the plurality of stimulation parameters from the external system 402. The implant storage device 532 stores values of the plurality of stimulation parameters, including parameters from one or more programs obtained using the programming modeling and closed loop programming techniques disclosed herein.

The power source 536 provides the implantable stimulator 404 with energy for its operation. In one embodiment, the power source 536 includes a battery. In one embodiment, the power source 536 includes a rechargeable battery and a battery charging circuit for charging the rechargeable battery. The implant telemetry circuit 534 may also function as a power receiver that receives power transmitted from external system 402 through an inductive couple.

In various embodiments, the sensing circuit 530, the stimulation output circuit 212, the stimulation control circuit 514, the implant telemetry circuit 534, the implant storage device 532, and the power source 536 are encapsulated in a hermetically sealed implantable housing. In various embodiments, the lead(s) 424 are implanted such that the electrodes 406 are placed on and/or around one or more targets to which the neurostimulation pulses are to be delivered, while the implantable stimulator 404 is subcutaneously implanted and connected to the lead(s) 424 at the time of implantation.

FIG. 6 illustrates an embodiment of a closed-loop programming system 602 used as part of an implantable neurostimulation system, such as the external system 402, with the closed-loop programming system 602 illustrated to receive data (e.g., commands, parameters, program selections, information) directly or indirectly from a program modeling system or input computing device (not shown in FIG. 6, but discussed with reference to FIG. 7, below) used to implement relevant closed-loop programming operations. The closed-loop programming system 602 represents an embodiment of the programming device 302, and includes an external telemetry circuit 640, an external storage device 616, a programming control circuit 620, a user interface device 610, a controller 630, and an external communication device 618, to effect programming of a connected neurostimulation device.

The closed-loop programming system 602 also includes a neurostimulation parameter generation circuit 660, coupled to a composite output processing circuit 662 and a model processing circuit 664, used to generate parameters or select programs for implementation with programming to the connected neurostimulation device. The model processing circuit 664 may implement logic to execute and operate a programming determination model (e.g., an AI model to dynamically generate parameter output values based on patient-specific values), such as to execute the model as discussed with reference to FIG. 7, below. The composite output processing circuit 662 may implement logic to determine and apply weighting within the model, such as discussed with reference to FIG. 7, below.

The operation of the neurostimulation parameter generation circuit 660, and specifically the use of the model and composite outputs from the model, further occurs based on the operations of the input and weighting control circuit 650. The input and weighting control circuit 650 includes a patient input processing circuit 652 to collect and identify patient input values relevant to input and weighting, such as discussed with reference to FIGS. 8 to 10, below. The input and weighting control circuit 650 also includes a therapy objective weighting circuit 654 to identify and calculate relevant weighting values for model execution and the production of composite outputs, based on the identified patient input values, such as discussed with reference to FIGS. 8 to 10, below.

The external telemetry circuit 640 provides the closed loop programming system 602 with wireless communication to and from another controllable device such as the implantable stimulator 404 via the telemetry link 426, including transmitting one or a plurality of stimulation parameters (including selected, identified, or modified stimulation parameters of a selected program) to the implantable stimulator 404. In one embodiment, the external telemetry circuit 640 also transmits power to the implantable stimulator 404 through inductive coupling.

The external communication device 618 may provide a mechanism to conduct communications with a programming information source, such as a data service, program modeling system, to receive program information, models, weighting logic, functionality controls, or the like, via an external communication link (not shown). The external communication device 618 and the programming information source may communicate using any number of wired or wireless communication mechanisms described in this document, including but not limited to IEEE 802.11 (Wi-Fi), Bluetooth, Infrared, and like standardized and proprietary wireless communications implementations. Although the external telemetry circuit 640 and the external communication device 618 are depicted as separate components within the closed-loop programming system 602, the functionality of both of these components may be integrated into a single communication chipset, circuitry, or device.

The external storage device 616 stores a plurality of existing neurostimulation waveforms, including definable waveforms for use as a portion of the pattern of the neurostimulation pulses, settings and setting values, other portions of a program, and related treatment efficacy indication values. In various embodiments, each waveform of the plurality of individually definable waveforms includes one or more pulses of the neurostimulation pulses, and may include one or more other waveforms of the plurality of individually definable waveforms. Examples of such waveforms include pulses, pulse blocks, pulse trains, and train groupings, and programs. The existing waveforms stored in the external storage device 616 can be definable at least in part by one or more parameters including, but not limited to the following: amplitude, pulse width, frequency, duration(s), electrode configurations, total charge injected per unit time, cycling (e.g., on/off time), waveform shapes, spatial locations of waveform shapes, pulse shapes, number of phases, phase order, interphase time, charge balance, and ramping.

The external storage device 616 may also store a plurality of individually definable fields that may be implemented as part of a program. Each waveform of the plurality of individually definable waveforms is associated with one or more fields of the plurality of individually definable fields. Each field of the plurality of individually definable fields is defined by one or more electrodes of the plurality of electrodes through which a pulse of the neurostimulation pulses is delivered and a current distribution of the pulse over the one or more electrodes. A variety of settings in a program (including settings changed as a result of evaluation with the dynamical information system and the dynamic models) may be correlated to the control of these waveforms and definable fields.

The programming control circuit 620 represents an embodiment of a programming control circuit 316 and may translate or generates the specific stimulation parameters or changes which are to be transmitted to the implantable stimulator 404, based on the results of the parameter generation circuit 660. The pattern may be defined using one or more waveforms selected from the plurality of individually definable waveforms (e.g., defined by a program) stored in an external storage device 616. In various embodiments, the programming control circuit 620 checks values of the plurality of stimulation parameters against safety rules to limit these values within constraints of the safety rules. In one embodiment, the safety rules are heuristic rules.

The user interface device 610 represents an embodiment of the user interface device 310 and allows the user (including a patient or clinician) to provide input relevant to therapy objectives, such as to implement the user interfaces discussed with reference to FIGS. 11A and 11B, below. The user interface device 610 includes a display screen 612, a user input device 614, and may implement or couple to the input and weighting control circuit 650. The display screen 612 may include any type of interactive or non-interactive screens, and the user input device 614 may include any type of user input devices that supports the various functions discussed in this document, such as a touchscreen, keyboard, keypad, touchpad, trackball, joystick, and mouse. The user interface device 610 may also allow the user to perform other functions where user interface input is suitable (e.g., to select, modify, enable, disable, activate, schedule, or otherwise define a program, sets of programs, provide feedback or input values, or perform other monitoring and programming tasks). Although not shown, the user interface 610 may also generate a visualization of such characteristics of device implementation or programming, and receive and implement commands to implement or revert the program and the neurostimulator operational values (including a status of implementation for such operational values). These commands and visualization may be performed in a review and guidance mode, status mode, or in a real-time programming mode.

The controller 630 can be a microprocessor that communicates with the external telemetry circuit 640, the external communication device 618, the external storage device 616, the programming control circuit 620, and the user interface device 610, via a bidirectional data bus. The controller 630 can be implemented by other types of logic circuitry (e.g., discrete components or programmable logic arrays) using a state machine type of design. As used in this disclosure, the term "circuitry" should be taken to refer to either discrete logic circuitry, firmware, or to the programming of a microprocessor.

Figure 7:
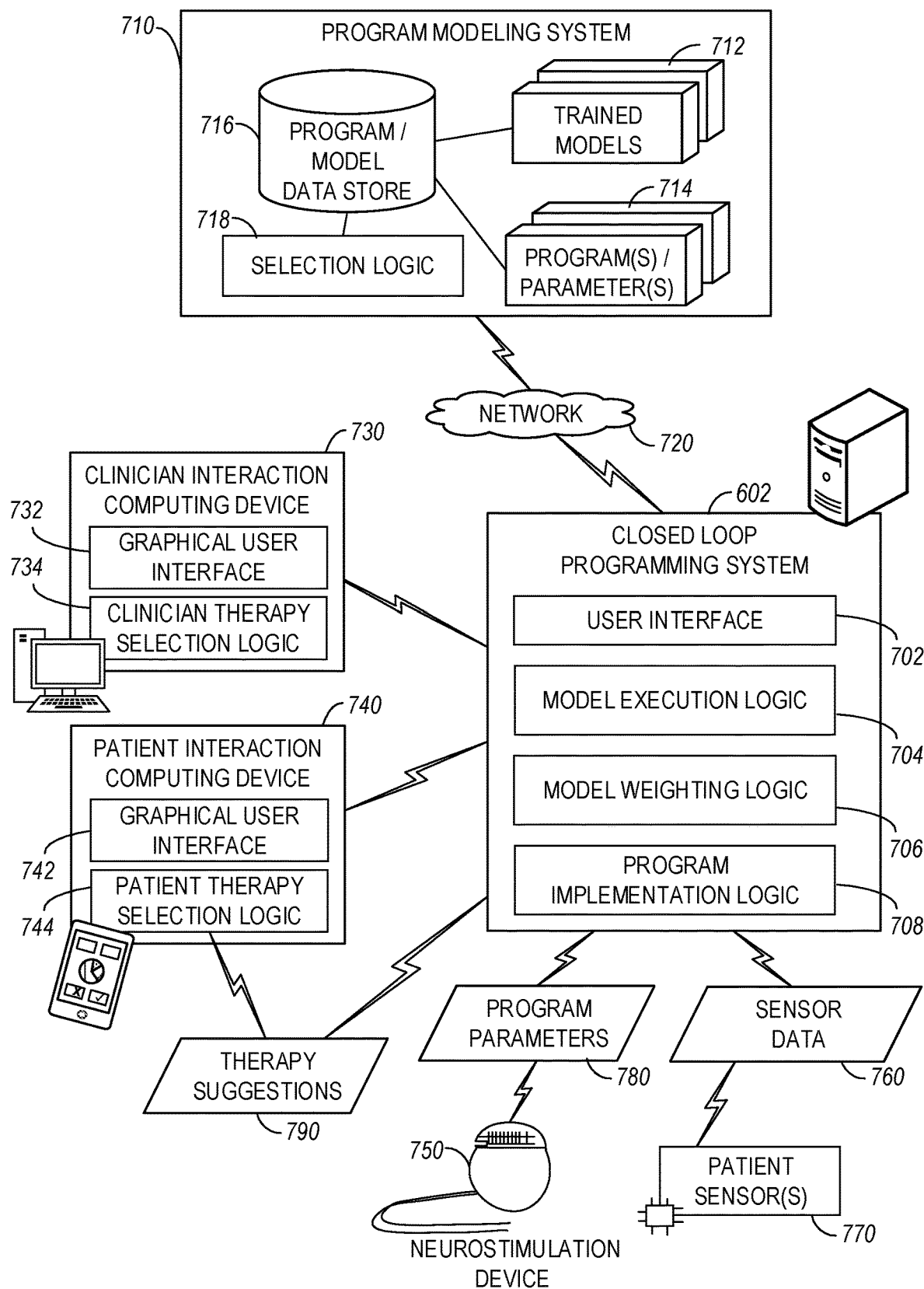
FIG. 7 illustrates, by way of example, an embodiment of data communicated among a closed-loop programming device, a program modeling system, and physician and patient interaction computing devices, for operation of a neurostimulation device based on user weighting of therapy objectives.

FIG. 7 illustrates, by way of example, an embodiment of data interactions among a closed-loop programming system 602, a program modeling system 710, and clinician and patient interaction computing devices 730, 740, for operation of a neurostimulation device 750 based on user weighting of therapy objectives. At a high level, the closed loop programming system 602 identifies and produces program parameters 780 which are implemented to the neurostimulation device (e.g., using the programming techniques discussed above). The closed loop programming system 602 produces these parameters through the execution and modification of a parameter generation model, such as an artificial intelligence model which considers closed-loop feedback to identify programming parameters for improved treatment of a patient using the neurostimulation device 750.

Specifically, the closed-loop programming system 602 operates program implementation logic 708 to generate programming parameters 780 in a closed loop fashion, based on the execution of models, user data inputs (e.g., patient and clinician inputs), sensor data inputs, and the like. The closed-loop programming system 602 may further include a user interface 702 which allows control, modification, selection, or specification of data values and data types from an administrative user, a clinician, a patient, or the like. The operation of the model is performed by model execution logic 704 to process inputs, evaluate data values, and generate outputs for the closed loop programming. The closed loop programming system 602 also includes model weighting logic 706 which adapts the execution of the model to arrive at different model outcomes.

The closed-loop programming system 602 may receive or access models, programs, parameters, algorithms, logic, or other aspects from use of a program modeling system 710. The program modeling system 710 is shown in FIG. 7 in the form of a computing device (e.g., a server) with the computing device being specially programmed to communicate, over a network 720, various trained models 712 and program or parameter data 714 that are retrieved from a program and model data store 716. In an example, the training of the models 712 may be controlled by a healthcare provider, a device manufacturer, or another third party. The program modeling system 710 may also implement selection logic 718 to respond to requests or inquiries for trained models, programs, parameter sets, such as from the closed-loop programming system 602. Other aspects of program settings, program modifications, constraints, rules, or like information related to programming or model operation may be communicated from the program modeling system 710 to the closed-loop programming system. It will be understood that other form factors and embodiments of the program modeling system 710, including in the integration of program modeling and selection logic into programming devices, data services, or information services, may also be provided.

The model weighting logic 706 of the closed-loop programming system 602 may apply weights determined from user inputs from a patient or clinician, with such user inputs being received via a clinician interaction computing device 730, or a patient interaction computing device 740. As discussed with further reference to FIGS. 10 to 11B, such user inputs may select and indicate therapy objectives to be addressed with the model operation. In an example, the patient interaction computing device 740 is a computing device (e.g., personal computer, tablet, smartphone) or other form of user-interactive device which receives and provides interaction with a patient using a graphical user interface 742 and therapy selection logic 744. Such interaction may be received via questionnaires, surveys, or selectable rating inputs, such as to collect input related to pain or satisfaction, or to identify a psychological or physiological state of the patient or treatment results.

The outputs in the graphical user interface 742 may be defined and interpreted using the logic 744, such as to convert various human-to-machine interactions to input that represents therapy indication values. Other form factors and interfaces such as smart speakers, audio interfaces, text interfaces, and the like may also be substituted for or augmented with the graphical user interface 742. The clinician interaction computing device 730 may include a graphical user interface 732 and therapy selection logic 734 with similar capabilities to the user interface 742 and selection logic 744, but adapted for use by a clinician (e.g., to provide enhanced functionality or features for physician control).

In an example, the closed loop programming system 602 generates, selects, or communicates therapy suggestions 790 to the patient interaction computing device 740 based on recommended or indicated therapy objectives. These therapy suggestions 790 may include a recommendation or identification of the type of therapies to apply, or may include suggested therapy objective values. The therapy suggestions 790 may provide other instructions, recommendations, or feedback (including clinician recommendations, behavioral modifications, etc., selected for the patient). The therapy suggestions 790 may provide relevant information based on the collection of sensor data 760 or other biopsychological/physiological state monitoring performed on the patient.

The closed loop programming system 602 may utilize sensor data 760 from one or more patient sensors 770 (e.g., wearables, sleep trackers, implantable devices, etc.) among one or more internal or external devices. The sensor data 760 is used by the closed loop programming system 602 as inputs to the executed models, to determine a customized and current state of the patient condition or treatment results. In various examples, the neurostimulation device 750 includes sensors which contribute to the sensor data 760 evaluated by the closed loop programming system.

In an example, the patient sensors 770 are biopsychosocial sensors or physiological sensors that sense one or more biopsychosocial signals indicative of the biopsychosocial factors (e.g., stress and/or mood biomarkers) or physical factors. Examples of such sensors include a facial recognition sensor to sense the patient's facial expression, a voice sensor (e.g., microphone) to sense the patient's voice, a sleep sensor to sense the patient's sleep state (e.g., for detecting lack of sleep), a heart rate sensor to sense the patient's heart rate, a blood pressure sensor to sense the patient's blood pressure, an electrodermal activity (EDA) sensor to sense the patient's EDA (e.g., galvanic skin response), and/or an electrochemical sensor to sense stress biomarkers from the patient's body fluids (e.g., enzymes and/or ions, such as lactate or cortisol from saliva or sweat). Other types or form factors of sensor devices may also be utilized.

Figure 8:
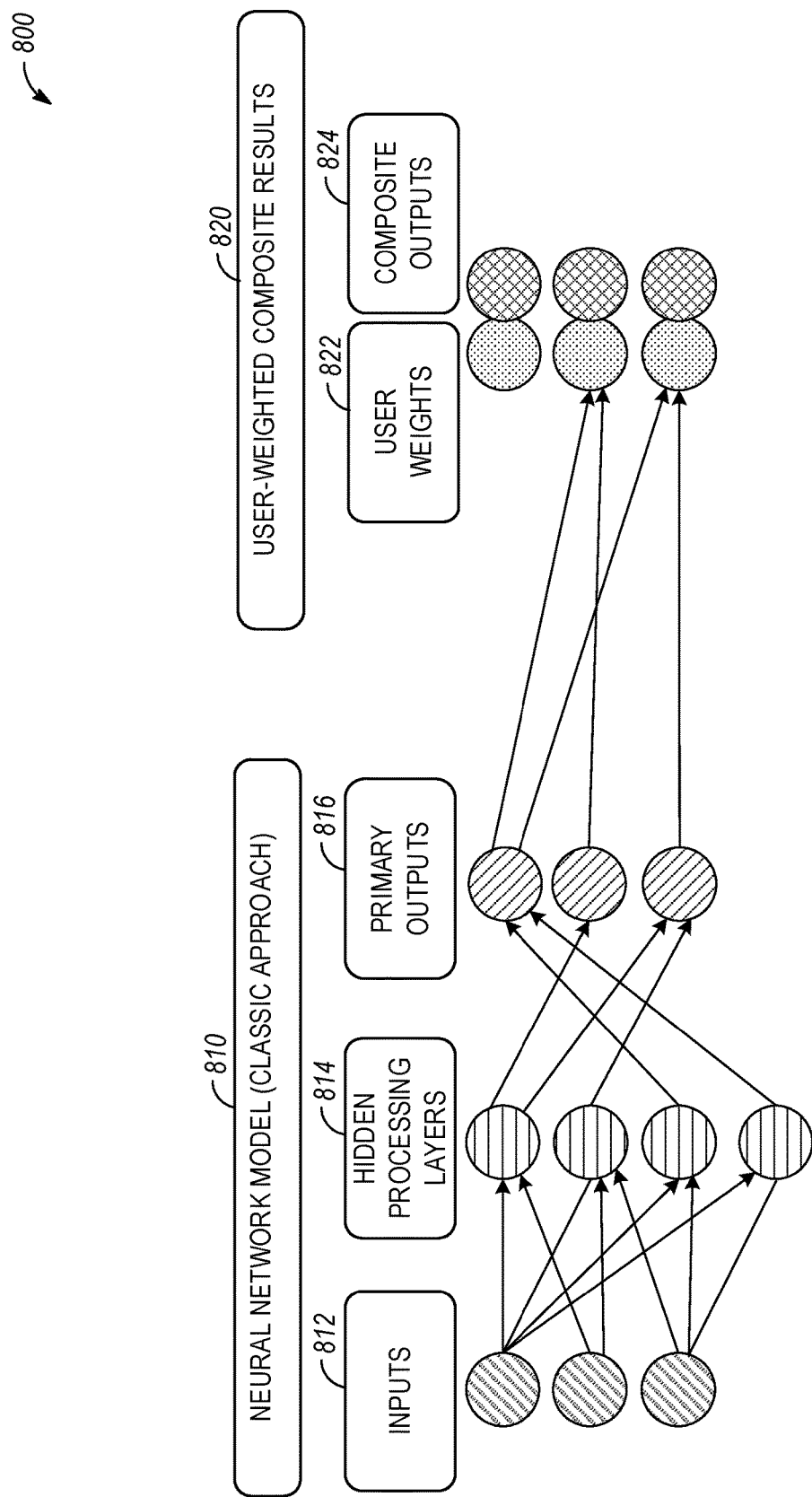
FIG. 8 illustrates, by way of example, an embodiment of processing layers of an artificial intelligence model adapted for producing composite outputs from user weighting of therapy objectives.

FIG. 8 illustrates, by way of example, an embodiment of processing layers of an artificial intelligence model 800 adapted for producing composite outputs from user weighting of therapy objectives. Specifically, the model 800 provides a high-level representation of a neural network model 810 and the pathways within such a model. This pathway may include nodes and vertices being defined based on relevant processing performed at each level of the neural network. For instance, depending on the values analyzed at the input layer 812 (e.g., sensor data values), one of various outputs at an output layer 816 may be reached. The neural network model 810, however, includes one or more intermediate processing layers 814, hidden, in the sense that they are not immediately observed, which provide intermediate nodes on a pathway defined between an input node layer and an output node layer. Although not shown, the neural network model 810 may include many other layers, weights, and pathways, depending on the type of network, the type and amount of training, the type of data being processed, and the types of algorithms used within processing layers. For instance, a "deep" neural network trained from deep learning methods may involve many layers of feature extraction and input/output pathways.

The processing layers of the model 800, provided by the neural network model 810 for closed-loop programming, are further enhanced with the use of weights and composite outputs being indicated by patient or clinician (user) input. As shown, user-weighted composite results 820 are generated from the application of user weights 822 to arrive at composite outputs 824. The particular composite output that is achieved therefore may be changed as a result of the weights from user input, even in a setting where most of the data pathways are dynamically determined from closed-loop data pathways.

As a simple example of the operation of the model 800, suppose that inputs to the neural network model 810 include data values from questionnaires, wearables, sleep trackers, and other sensors and patient input. The primary outputs produced by the output layer 816 may include programming parameter values which are designed to address pain reduction, medication management (e.g., opioid reduction, change in type or dosage of medication, etc.), or sleep improvement. The use of the user weights 822 and the generation of composite outputs 824 may result in composite outputs for: Pain and Sleep Improvement; Pain and Opioid Reduction; Sleep Improvement and Opioid Reduction; or any suitable combination of the primary outputs. These composite outputs may still include programming parameter values, but which are balanced or modified to address multiple of the therapy objectives.

Figure 9:
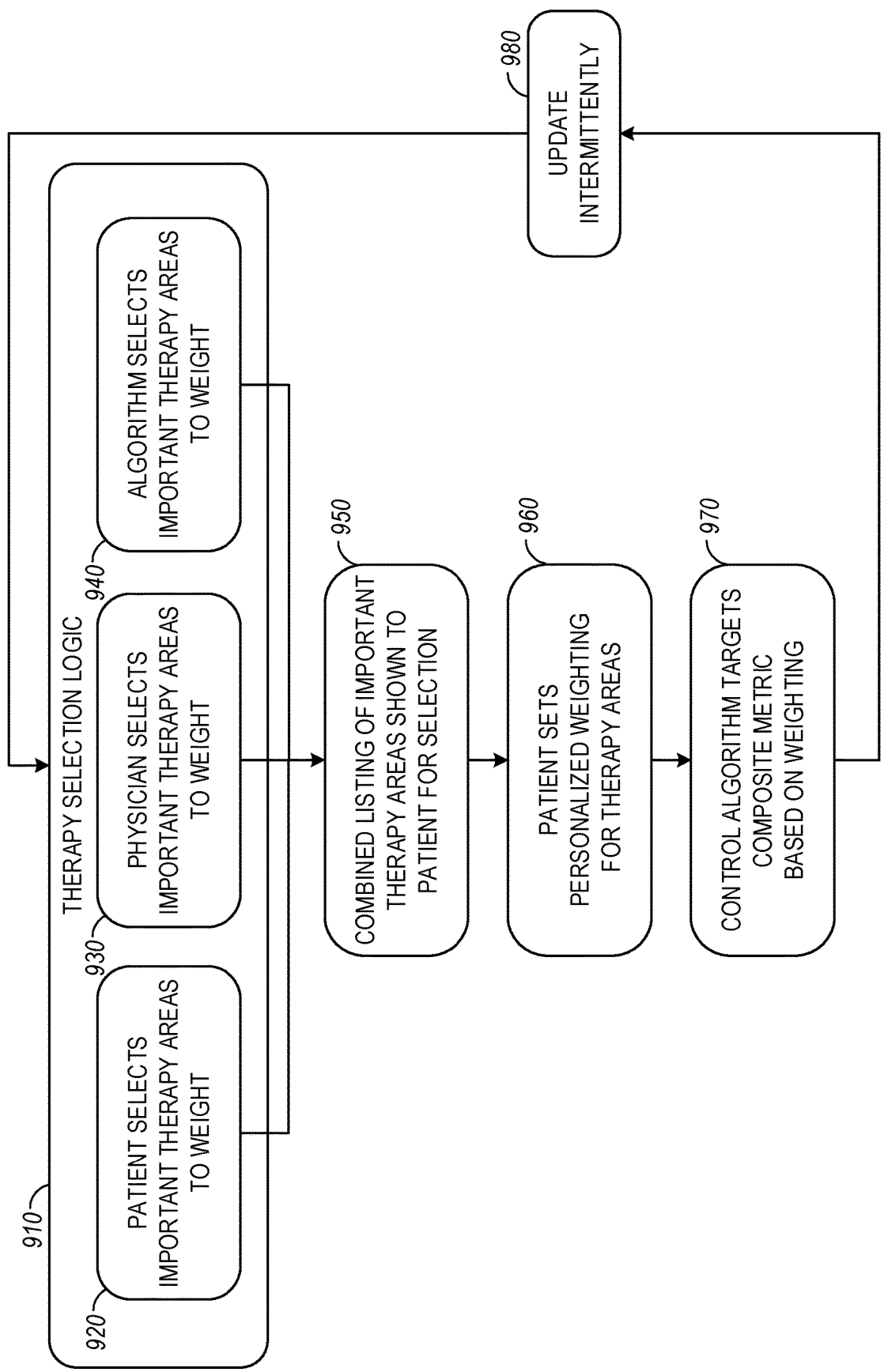
FIG. 9 illustrates, by way of example, an embodiment of a data operation flow for closed-loop programming adjustment based on implementing composite outputs from user weighting of therapy objectives.

FIG. 9 illustrates, by way of example, an embodiment of a data operation flow for closed-loop programming adjustment, based on implementing composite outputs from user weighting of therapy objectives. This flow is first directed by therapy selection logic 910. The therapy selection logic 910 may be implemented by one or more of: a patient selection 920 of one or more therapy areas to weight; a clinician (e.g., physician) selection 930 of therapy areas to weight; or an algorithm selection 940 of therapy areas to weight. For example, the therapy selection logic 910 may exclude or limit certain types of therapy or therapy objectives, such as types of therapy which would be clinically inappropriate or detrimental to the patient; likewise, the therapy selection logic 910 may be used to emphasize certain types of therapy to address identified concerns.

The data operation flow continues with a compilation of a combined listing of therapy areas at 950, narrowed or identified from the selected therapies or therapy objectives at 920, 930, 940). This listing of therapy areas may be provided to a patient for further selection and input, and specification of therapy objectives. Using this listing of therapy areas, the patient sets personalized weighting or input values for the respective therapy areas, at 960. The closed-loop processing system then applies the personalized weighting or input values with an algorithm, at 970, to produce a composite metric of programming values from the model outputs. The closed-loop processing system may perform further updates at 980, intermittently or on a scheduled basis, to identify additional therapy areas for processing or consideration.

Figure 10:
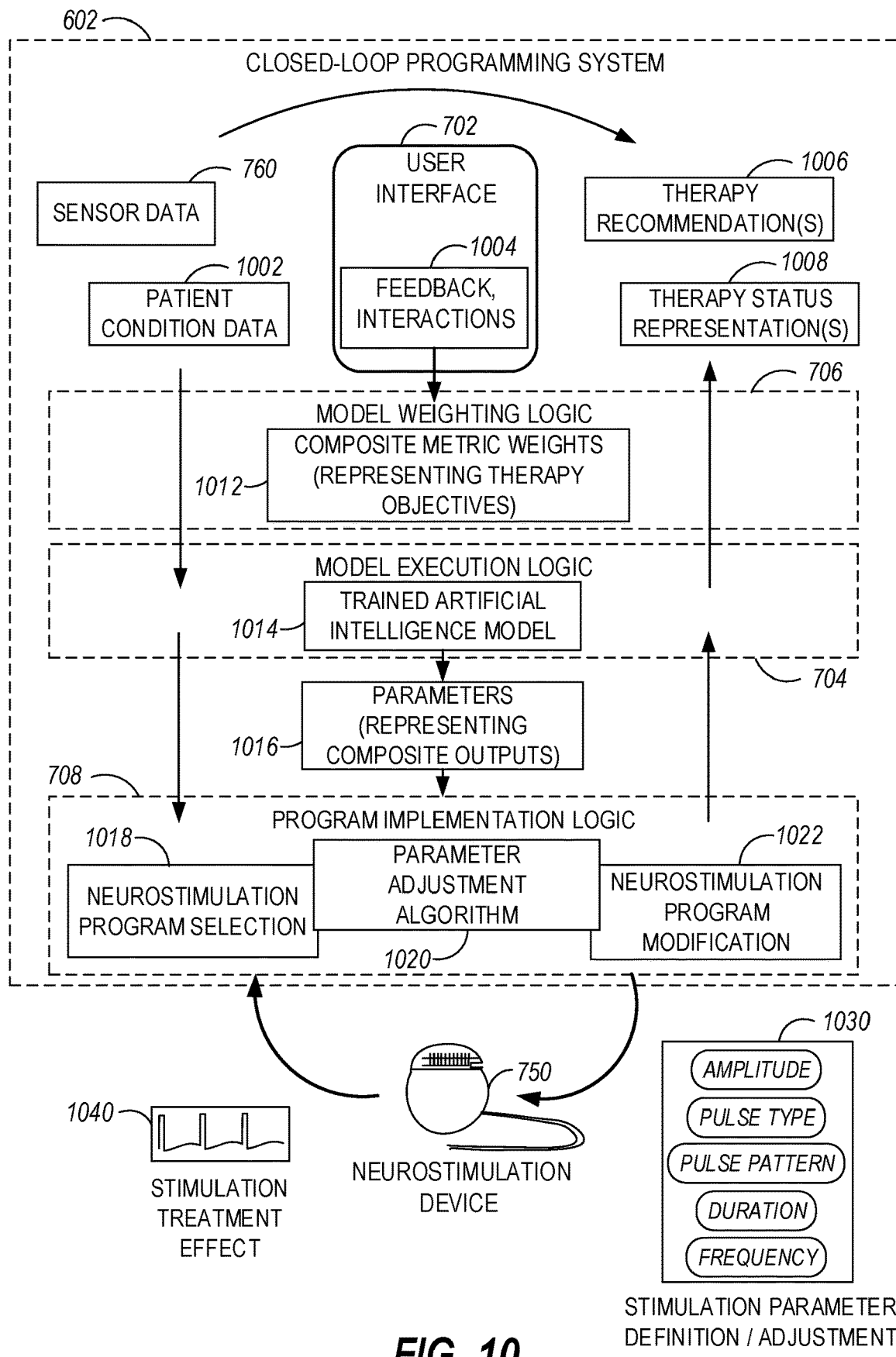
FIG. 10 illustrates, by way of example, an embodiment of a closed-loop processing flow for implementing neurostimulation treatment of a human patient, using weighting of composite outputs for therapy objectives in a neurostimulation programming model.

FIG. 10 illustrates, by way of example, an embodiment of a closed-loop processing flow for implementing neurostimulation treatment of a human patient, using weighting of composite outputs for therapy objectives in a neurostimulation programming model. In addition to the sensor data 760 being processed by the closed-loop programming system 602, FIG. 10 also depicts the consideration of patient condition data 1002 which may be derived from clinician or patient data outputs. In addition to the parameter and program changes provided by the closed-loop programming system 602, other outputs may be determined or influenced, such as one or more therapy recommendations 1006, one or more therapy status representations 1008, and other outputs.

The closed loop programming system 602 is depicted as receiving feedback and interactions 1004 within its user interface 702, which are processed to identify composite metric weights 1012 by the model weighting logic 706. The composite metric weights 1012 are then utilized by the model execution logic, to produce parameters that represent composite outputs from the trained artificial intelligence model 1014. These parameters 1016 are then provided to the program implementation logic 708.

The program implementation logic 708 may be implemented by a parameter adjustment algorithm 1020, which affects a neurostimulation program selection 1018 or a neurostimulation program modification 1022. For instance, some parameter changes may be implemented by a simple modification to a program operation; other parameter changes may require a new program to be deployed. The results of the parameter or program changes or selection results in definition or adjustment to various stimulation parameters 1030 at the neurostimulation device 750, causing a different or new stimulation treatment effect 1040.

Figure 11B:
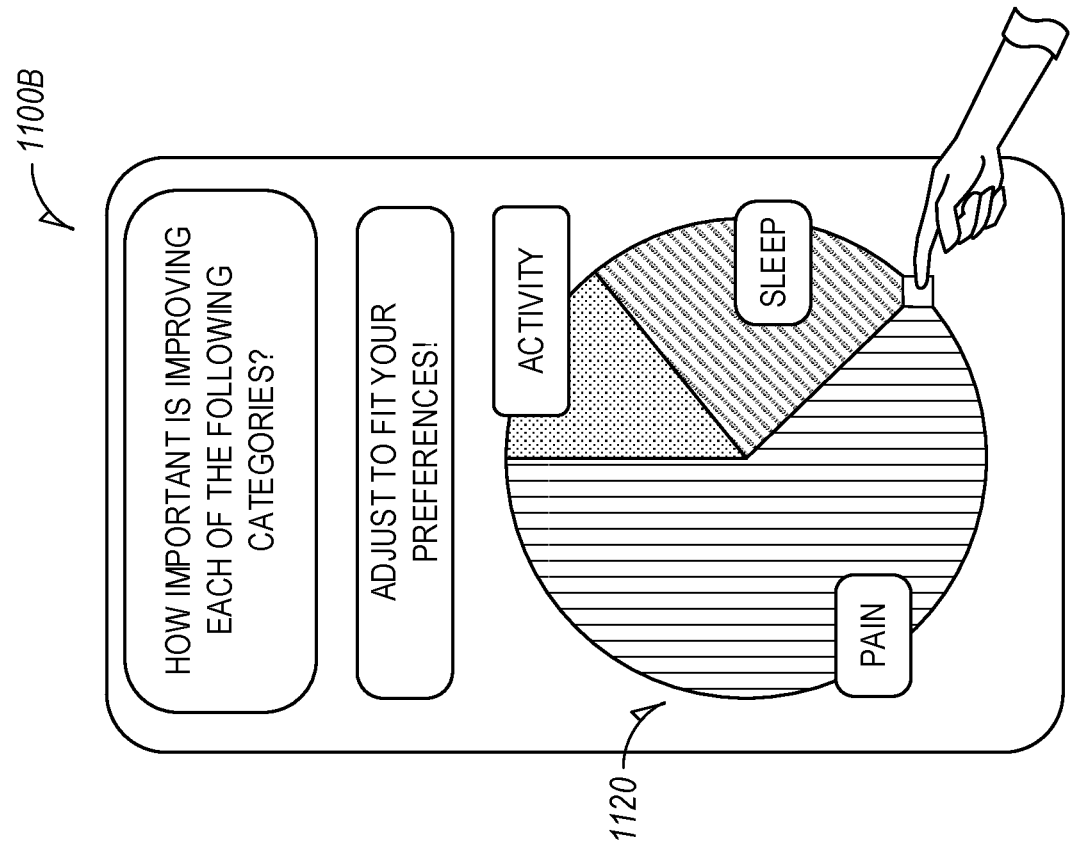
FIGS. 11A and 11B illustrate, by way of example, embodiments of graphical user interfaces adapted to receive patient inputs indicating therapy objectives for use in a neurostimulation programming model.
Figure 11A:
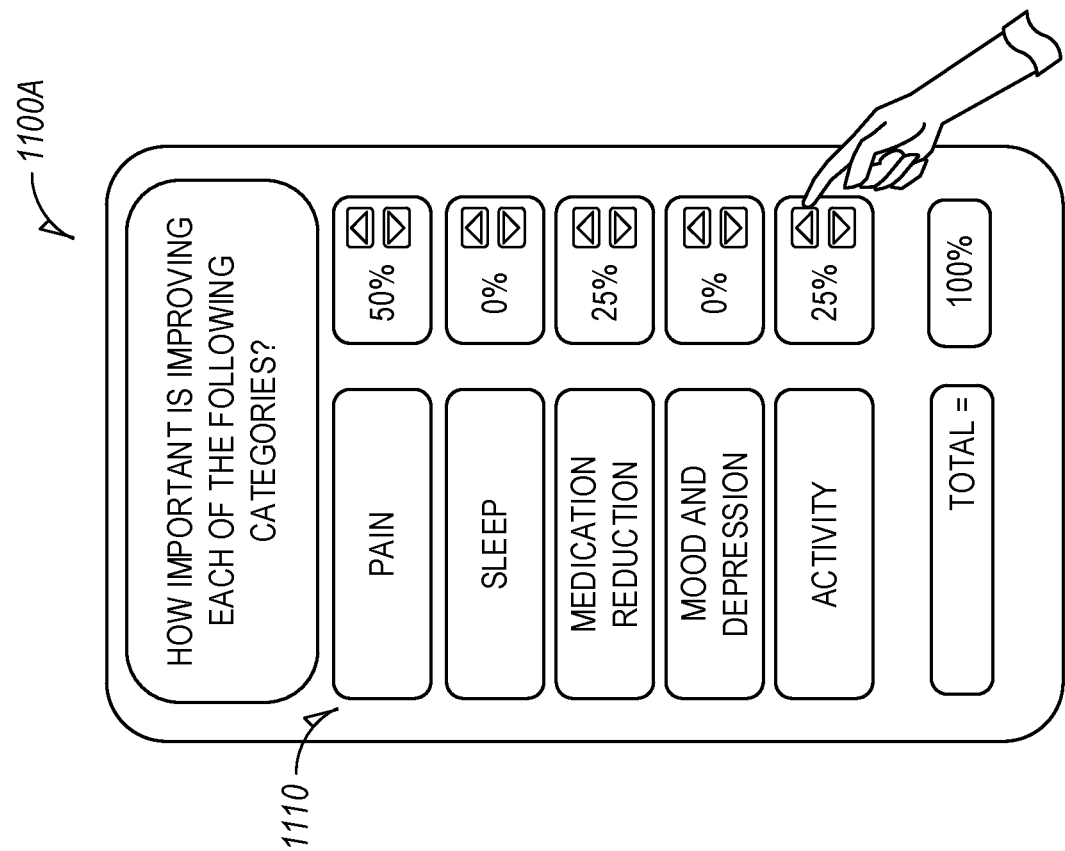

FIGS. 11A and 11B illustrate, by way of example, embodiments of graphical user interfaces 1100A, 1100B, each adapted to receive patient inputs indicating therapy objectives for use in a neurostimulation programming model. A first example of graphical interface 1100A shows user input of numeric values 1110 corresponding to multiple therapy areas (e.g., therapy areas identified using therapy selection logic 910). The user input of numeric values may be a scaled value, such as from 0 to 100. Other types of values, such as rankings, or binary indications, may also be used. A second example of graphical interface 1100B, depicts a pie chart 1120 indicating values divided among multiple therapy areas. Other types of user inputs or values, which are used to identify therapy objectives and areas for weighting, may also be used.

Figure 12:
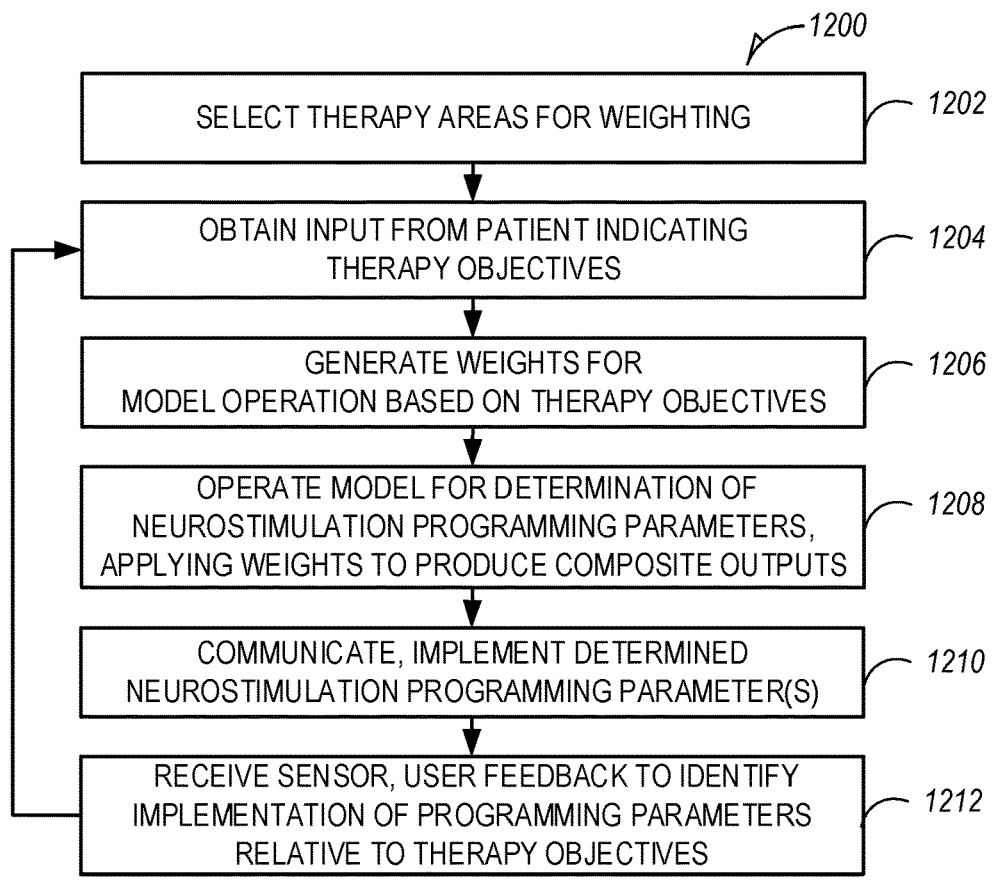
FIG. 12 illustrates, by way of example, a flowchart of a method implemented by a system or device to generate programming values of an implantable electrical neurostimulation device, by producing composite outputs from a neurostimulation programming model.

FIG. 12 illustrates, by way of example, an embodiment of a processing method 1200 implemented by a system or device for use to adjust programming of an implantable electrical neurostimulation device based on trust dynamics. For example, the processing method 1200 can be embodied by electronic operations performed by one or more computing systems or devices that are specially programmed to implement the input collection, model execution and model weighting, and neurostimulation programming functions described herein. In specific examples, the operations of the method 1200 may be implemented through the systems and data flows depicted above in FIGS. 6 to 11.

In an example, the method 1200 begins with the selection of therapy areas for weighting (operation 1202), such as is discussed above with reference to the therapy selection logic 910 in FIG. 9. For instance, the multiple therapy objectives may be selected from a larger set of available therapy objectives, and as the multiple therapy objectives are selected based on: patient identification of therapy types, clinician identification of therapy types, or algorithm identification of therapy types.

The method 1200 continues by obtaining input provided from a patient or other user (e.g., clinician) which indicates one or multiple therapy objectives for analysis (operation 1204). These therapy objectives may be provided from among the selected therapy areas (of operation 1202). In an example, the input provides a rating value associated with each of the therapy objectives, and these rating values are used to determine values of identified weights for use in the programming model, in the following operations. The inputs may be provided in graphical user interface, such as that discussed with reference to FIGS. 11A and 11B, indicated above.

The method 1200 continues by identifying weights for use in a neurostimulation programming model, based on the therapy objectives indicated in the input (operation 1206). This neurostimulation programming model is trained or otherwise configured to determine parameter outputs for programming of the neurostimulation device. The method 1200 continues by applying weights, within the operation of the neurostimulation programming model, to produce programming parameters for composite outputs of the programming model (operation 1208). The identification and selection of weights may be performed as discussed with reference to the processing techniques in FIGS. 7 and 10, indicated above. In an example, the programming model is implemented as an artificial neural network or as a machine learning classifier. For instance, a neural network may be implemented as a deep neural network that includes a plurality of intermediate processing layers, as the identified weights are applied at an output layer of the deep neural network to produce the composite outputs. For instance, the overall arrangement of the model may follow that described with reference to FIG. 8, above, or variations to such models.

Further operations and feedback as part of the method 1200 may continue with the receipt of sensor data, user feedback data, or other data values, which can be used to identify the accuracy or efficacy of implementation of the programming parameters relative to the therapy objectives (operation 1212). The use of this data may provide a closed-loop adjustment of device programming operations, which may involve the repeating of the operations 1204-1210 for a subsequent evaluation of therapy objectives, generation of weights, operation of a programming model, and implementation of identified programming parameters, adjusted based on the received data in operation 1212. As a result, updated weights for use in additional executions of the model may be generated and used, while still considering user input in a closed-loop system.

Figure 13:
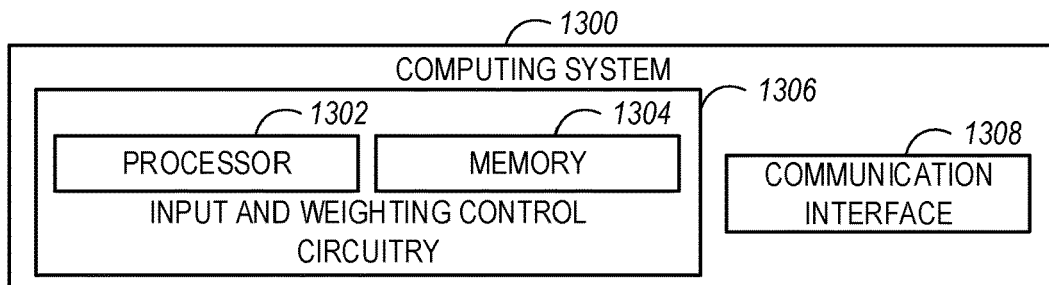
FIG. 13 illustrates, by way of example, a block diagram of an embodiment of a computing system implementing input and weighting control processing circuitry, to control operation and output of a neurostimulation programming model.

FIG. 13 illustrates, by way of example, a block diagram of an embodiment of a system 1300 (e.g., a computing system) implementing input and weighting control to modify operation and output of a neurostimulation programming mode. The system 1300 may be integrated as or as part of a remote control device, patient programmer device, clinician programmer device, program modeling system, or other external device, usable for the adjustment of neurostimulation programming with the programming model approaches discussed herein. In some examples, the system 1300 may be a networked device connected via a network (or combination of networks) to a programming device or programming service using a communication interface 1308. The network may include local, short-range, or long-range networks, such as Bluetooth, cellular, IEEE 802.11 (Wi-Fi), or other wired or wireless networks.

The system 1300 includes a processor 1302 and a memory 1304, which can be optionally included as part of input and weighting control circuitry 1306. The processor 1302 may be any single processor or group of processors that act cooperatively. The memory 1304 may be any type of memory, including volatile or non-volatile memory. The memory 1304 may include instructions, which when executed by the processor 1302, cause the processor 1302 to implement the features of the user interface, or to enable other features of the input and weighting control circuitry 1306. Thus, electronic operations in the system 1300 may be performed by the processor 1302 or the circuitry 1306.

For example, the processor 1302 or circuitry 1306 may implement any of the features of the method 1200 (including operations 1202, 1204, 1206) to obtain and process data, to produce weighting or weighting results, from user-input therapy objectives, for composite outputs of a neurostimulation parameter model. The system 1300 may save, communicate, or cause implementation of the weighting, directly or indirectly. It will be understood that the processor 1302 or circuitry 1306 may also implement other aspects of the logic and processing described above with reference to FIGS. 6-12, for use in a closed-loop system.

Figure 14:
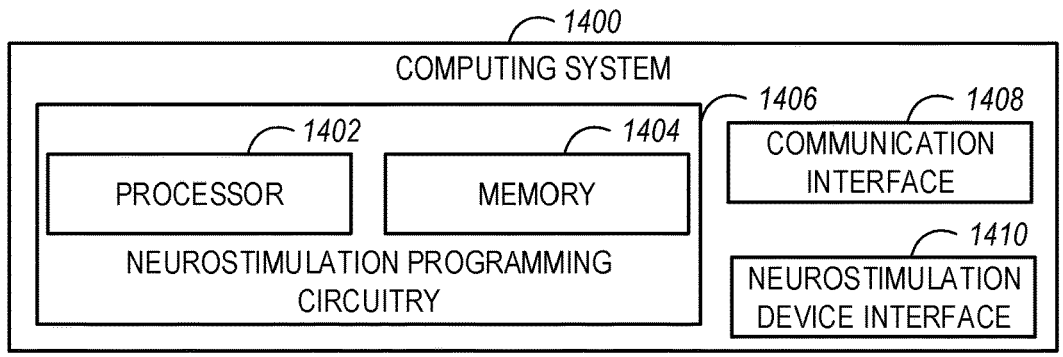
FIG. 14 illustrates, by way of example, a block diagram of an embodiment of a computing system implementing neurostimulation programming circuitry, to cause programming of an implantable electrical neurostimulation device.

FIG. 14 illustrates, by way of example, a block diagram of an embodiment of a system 1400 (e.g., a computing system) implementing neurostimulation programming circuitry 1406 to cause programming of an implantable electrical neurostimulation device, for accomplishing the therapy objectives in a human subject as discussed herein. The system 1400 may be operated by a clinician, a patient, a caregiver, a medical facility, a research institution, a medical device manufacturer or distributor, and embodied in a number of different computing platforms. The system 1400 may be a remote control device, patient programmer device, program modeling system, or other external device, including a regulated device used to directly implement programming commands and modification with a neurostimulation device. In some examples, the system 1400 may be a networked device connected via a network (or combination of networks) to a computing system operating a user interface computing system using a communication interface 1408. The network may include local, short-range, or long-range networks, such as Bluetooth, cellular, IEEE 802.11 (Wi-Fi), or other wired or wireless networks.

The system 1400 includes a processor 1402 and a memory 1404, which can be optionally included as part of neurostimulation programming circuitry 1406. The processor 1402 may be any single processor or group of processors that act cooperatively. The memory 1404 may be any type of memory, including volatile or non-volatile memory. The memory 1404 may include instructions, which when executed by the processor 1402, cause the processor 1402 to implement the features of the neurostimulation programming circuitry 1406. Thus, the electronic operations in the system 1400 may be performed by the processor 1402 or the circuitry 1406.

The processor 1402 or circuitry 1406 may implement any of the features of the method 1200 (including operations 1210) to identify neurostimulation programming parameters, and implement (e.g., save, persist, activate, control) the programming parameters or relevant programs in the neurostimulation device, with use of a neurostimulation device interface 1410. The processor 1402 or circuitry 1406 may further provide data and commands to assist the processing and implementation of the programming using communication interface 1408. It will be understood that the processor 1402 or circuitry 1406 may also implement other aspects of the programming devices and device interfaces described above with reference to FIGS. 6-11.

Figure 15:
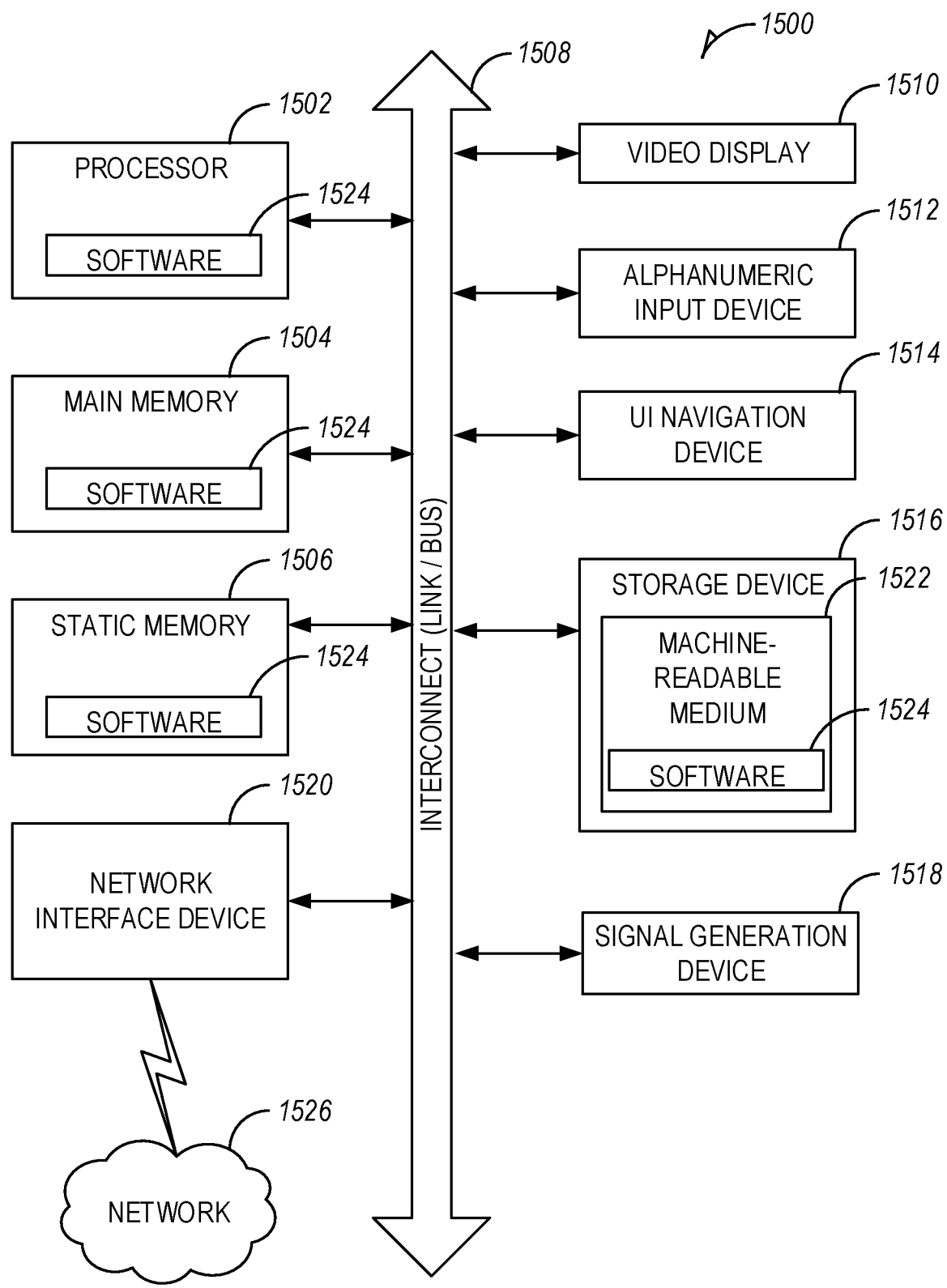
FIG. 15 is a block diagram illustrating a machine in the example form of a computer system, within which a set or sequence of instructions may be executed to cause the machine to perform any one of the methodologies discussed herein, according to an example embodiment.

FIG. 15 is a block diagram illustrating a machine in the example form of a computer system 1500, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer (PC), a tablet PC, a hybrid tablet, a personal digital assistant (PDA), a mobile telephone, an implantable pulse generator (IPG), an external remote control (RC), a User's Programmer (CP), or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

Example computer system 1500 includes at least one processor 1502 (e.g., a central processing unit (CPU), a graphics processing unit (GPU) or both, processor cores, compute nodes, etc.), a main memory 1504 and a static memory 1506, which communicate with each other via a link 1508 (e.g., bus). The computer system 1500 may further include a video display unit 1510, an alphanumeric input device 1512 (e.g., a keyboard), and a user interface (UI) navigation device 1514 (e.g., a mouse). In one embodiment, the video display unit 1510, input device 1512 and UI navigation device 1514 are incorporated into a touch screen display. The computer system 1500 may additionally include a storage device 1516 (e.g., a drive unit), a signal generation device 1518 (e.g., a speaker), a network interface device 1520, and one or more sensors (not shown), such as a global positioning system (GPS) sensor, compass, accelerometer, or other sensor. It will be understood that other forms of machines or apparatuses (such as PIG, RC, CP devices, and the like) that are capable of implementing the methodologies discussed in this disclosure may not incorporate or utilize every component depicted in FIG. 15 (such as a GPU, video display unit, keyboard, etc.).

The storage device 1516 includes a machine-readable medium 1522 on which is stored one or more sets of data structures and instructions 1524 (e.g., software) embodying or utilized by any one or more of the methodologies or functions described herein. The instructions 1524 may also reside, completely or at least partially, within the main memory 1504, static memory 1506, and/or within the processor 1502 during execution thereof by the computer system 1500, with the main memory 1504, static memory 1506, and the processor 1502 also constituting machine-readable media.

While the machine-readable medium 1522 is illustrated in an example embodiment to be a single medium, the term "machine-readable medium" may include a single medium or multiple media (e.g., a centralized or distributed database, and/or associated caches and servers) that store the one or more instructions 1524. The term "machine-readable medium" shall also be taken to include any tangible (e.g., non-transitory) medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 1524 may further be transmitted or received over a communications network 1526 using a transmission medium via the network interface device 1520 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or 5G networks). The term "transmission medium" shall be taken to include any intangible medium that is capable of storing, encoding, or carrying instructions for execution by the machine, and includes digital or analog communications signals or other intangible medium to facilitate communication of such software.

The above detailed description is intended to be illustrative, and not restrictive. The scope of the disclosure should, therefore, be determined with references to the appended claims, along with the full scope of equivalents to which such claims are entitled.

What is claimed is:

1. A system for use to generate programming values for a neurostimulation device, the system comprising:
    at least one processor and at least one memory;
    input and weighting control circuitry, operable with the processor and the memory, the input and weighting control circuitry configured to:
        obtain input indicating multiple therapy objectives, the multiple therapy objectives being provided by a human patient for treatment with the neurostimulation device;
        operate an artificial intelligence neurostimulation programming model, the programming model configured to determine parameter outputs for programming of the neurostimulation device;
        identify user weights for use at an output layer of the programming model, wherein the user weights provide values to combine the multiple therapy objectives provided by the human patient; and
        generate a composite output from the programming model, by applying the user weights at the output layer to a combination of the parameter outputs of the programming model, to produce a user-weighted result of the parameter outputs from the programming model;
    neurostimulation programming circuitry, operable with the at least one processor and the at least one memory, configured to:
        generate parameter programming values to program the neurostimulation device, based on the composite output from the programming model; and
    communication circuitry, in operation with the neurostimulation programming circuitry, configured to:
        transmit at least one communication signal to the neurostimulation device, the at least one communication signal to configure the neurostimulation device with the parameter programming values to perform the neurostimulation treatment of the human patient according to the multiple therapy objectives.

2. The system of claim 1, further comprising the neurostimulation device, wherein the neurostimulation programming circuitry is further configured to implement the parameter programming values in at least one selectable program of the neurostimulation device.

3. The system of claim 1, wherein the programming model is implemented as an artificial neural network or as a machine learning classifier.

4. The system of claim 1, the input and weighting control circuitry further configured to:

obtain user feedback, the user feedback indicating user-indicated efficacy of the programming of the neurostimulation device using the composite output, based on the multiple therapy objectives; and generate updated weights for use in the programming model, the updated weights produced from changes to the user weights based on the user feedback.

5. The system of claim 1, the input and weighting control circuitry further configured to:

obtain sensor data feedback, the sensor data feedback indicating a measurement related to one or more of the multiple therapy objectives; and generate updated weights for use in the programming model, the updated weights produced from changes to the user weights based on the sensor data feedback.

6. The system of claim 1, wherein the input further indicates a rating value associated with each of the multiple therapy objectives, wherein the respective rating values associated with the multiple therapy objectives are used to determine values of the user weights.

7. The system of claim 1, wherein the multiple therapy objectives are selected from a set of available therapy objectives, and wherein the multiple therapy objectives are selected based on an identification including one or more of:

patient identification of one or more therapy types to produce with the programming model, clinician identification of one or more therapy types to produce with the programming model, or algorithm identification of one or more therapy types to produce with the programming model.

8. The system of claim 1, wherein the multiple therapy objectives include a combination of at least two therapy types selected from among: pain management, sleep quality, medication management, mood improvement, depression reduction, or activity capabilities.

9. The system of claim 1, the input and weighting control circuitry further configured to:

obtain input indicating variations to the multiple therapy objectives, the variations to the multiple therapy objectives being provided by a clinician associated with treatment of the human patient; and perform balancing of the multiple therapy objectives with the variations to the multiple therapy objectives, based on a comparison between the variations to the multiple therapy objectives provided by the clinician and the multiple therapy objectives provided by the human patient;

wherein the user weights are produced from the balancing of the multiple therapy objectives with the variations to the multiple therapy objectives; and wherein the input provided by the clinician is obtained in a clinician graphical user interface, and wherein the input provided by the human patient is obtained in a patient graphical user interface.

10. The system of claim 1, wherein the composite output is utilized as a parameter of a neurostimulation program for the neurostimulation device, and wherein the neurostimulation programming circuitry is further configured to:

identify programming values for at least one neurostimulation programming parameter in the neurostimulation program based on the composite output;

wherein the identified programming values specify operation of the neurostimulation program for one or more of: pulse patterns, pulse shapes, a spatial location of pulses, waveform shapes, or a spatial location of waveform shapes, for modulated energy provided with a plurality of leads of the neurostimulation device.

11. A method for producing programming values for a neurostimulation device, the method comprising a plurality of operations executed with at least one processor of an electronic device, the plurality of operations comprising:

receiving input indicating multiple therapy objectives, the therapy objectives being provided by a human patient for treatment with the neurostimulation device;

executing an artificial intelligence neurostimulation programming model, the programming model configured to determine parameter outputs for programming of the neurostimulation device;

identifying user weights for use at an output layer of the programming model, wherein the user weights provide values to combine the multiple therapy objectives provided by the human patient;

generating a composite output from the programming model, by applying the user weights at the output layer to a combination of the parameter outputs of the programming model, to produce a user-weighted result of the parameter outputs from the programming model;

generating parameter programming values to program the neurostimulation device, based on the composite output from the programming model; and transmitting at least one communication signal to the neurostimulation device, the at least one communication signal to configure the neurostimulation device with the parameter programming values to perform the neurostimulation treatment of the human patient according to the multiple therapy objectives.

12. The method of claim 11, the operations further comprising:

causing the neurostimulation device to implement the parameter programming values in at least one selectable program of the neurostimulation device.

13. The method of claim 11, wherein the programming model is implemented as an artificial neural network or as a machine learning classifier.

14. The method of claim 11, the operations further comprising:

obtaining user feedback, the user feedback indicating user-indicated efficacy of the programming of the neurostimulation device using the composite output, based on the multiple therapy objectives; and generating updated weights for use in the programming model, the updated weights produced from changes to the user weights based on the user feedback.

15. The method of claim 11, obtaining sensor data feedback, the sensor data feedback indicating a measurement related to one or more of the multiple therapy objectives; and generating updated weights for use in the programming model, the updated weights produced from changes to the user weights based on the sensor data feedback.

16. The method of claim 11, wherein the input further indicates a rating value associated with each of the multiple therapy objectives, wherein the respective rating values associated with the multiple therapy objectives are used to determine values of the user weights.

17. The method of claim 11, wherein the multiple therapy objectives are selected from a set of available therapy objectives, and wherein the multiple therapy objectives are selected based on an identification including one or more of:

patient identification of one or more therapy types to produce with the programming model, clinician identification of one or more therapy types to produce with the programming model, or algorithm identification of one or more therapy types to produce with the programming model.

18. The method of claim 11, wherein the multiple therapy objectives include a combination of at least two therapy types selected from among:
   pain management, sleep quality, medication management, mood improvement, depression reduction, or activity capabilities.

19. The method of claim 11, the operations further comprising:
   obtaining input indicating variations to the multiple therapy objectives, the variations to the multiple therapy objectives being provided by a clinician associated with treatment of the human patient; and
   performing balancing of the multiple therapy objectives with the variations to the multiple therapy objectives, based on a comparison between the variations to the multiple therapy objectives provided by the clinician and the multiple therapy objectives provided by the human patient;
   wherein the user weights are produced from the balancing of the multiple therapy objectives with the variations to the multiple therapy objectives; and
   wherein the input provided by the clinician is obtained in a clinician graphical user interface, and wherein the input provided by the human patient is obtained in a patient graphical user interface.

20. The method of claim 11, wherein the composite output is utilized as a parameter of a neurostimulation program for the neurostimulation device, the operations further comprising:
   identifying programming values for at least one neurostimulation programming parameter in the neurostimulation program based on the composite output;
   wherein the identified programming values specify operation of the neurostimulation program for one or more of: pulse patterns, pulse shapes, a spatial location of pulses, waveform shapes, or a spatial location of waveform shapes, for modulated energy provided with a plurality of leads of the neurostimulation device.

* * * * *